(12) United States Patent
Chun et al.

(10) Patent No.: US 10,106,797 B2
(45) Date of Patent: Oct. 23, 2018

(54) METHODS FOR SUPPRESSING ADIPOCYTE DIFFERENTIATION

(71) Applicant: SEOUL NATIONAL UNIVERSITY R&DB FOUNDATION, Seoul (KR)

(72) Inventors: Yang-Sook Chun, Seoul (KR); Hyoung Sook Park, Seoul (KR); Jong-Wan Park, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 13 days.

(21) Appl. No.: 14/905,298

(22) PCT Filed: Jul. 18, 2014

(86) PCT No.: PCT/KR2014/006527
§ 371 (c)(1),
(2) Date: Jan. 15, 2016

(87) PCT Pub. No.: WO2015/009094
PCT Pub. Date: Jan. 22, 2015

(65) Prior Publication Data
US 2016/0160219 A1 Jun. 9, 2016

(30) Foreign Application Priority Data

Jul. 18, 2013 (KR) .................. 10-2013-0084540

(51) Int. Cl.
| | | |
|---|---|---|
| *A61K 38/53* | (2006.01) | |
| *A61K 39/395* | (2006.01) | |
| *C07K 16/40* | (2006.01) | |
| *C12N 15/113* | (2010.01) | |
| *G01N 33/50* | (2006.01) | |
| *G01N 33/68* | (2006.01) | |

(52) U.S. Cl.
CPC .......... *C12N 15/1137* (2013.01); *A61K 38/53* (2013.01); *A61K 39/3955* (2013.01); *C07K 16/40* (2013.01); *C12N 15/113* (2013.01); *G01N 33/5023* (2013.01); *G01N 33/5044* (2013.01); *G01N 33/5073* (2013.01); *G01N 33/6875* (2013.01); *C12N 2310/11* (2013.01); *C12N 2310/14* (2013.01); *G01N 2333/70567* (2013.01); *G01N 2500/00* (2013.01)

(58) Field of Classification Search
CPC .... A61K 38/40; A61K 39/3955; C07K 16/40; C12N 15/113; C12N 15/1137; C12N 2310/11; C12N 2310/14
See application file for complete search history.

(56) References Cited

FOREIGN PATENT DOCUMENTS

| KR | 10-1232872 B1 | 2/2013 |
| WO | WO2011/098262 | * 8/2011 |

OTHER PUBLICATIONS

Vassilev, L.T. et al. In vivo activation of the p53 pathway by small-molecule antagonists of MDM2. Science, 2004, vol. 303, p. 884-848.*
Adan, "Mechanisms underlying current and future anti-obesity drugs", Trends in Neurosciences, vol. 36, No. 2, pp. 133-140, (2013).
Hallenborg et al., "Mdm2 controls CREB-dependent transactivation and initiation of adipocyte differentiation", Cell Death and Differentiation, vol. 19, pp. 1381-1389, (2012).
Molchadsky et al., "p53 Plays a Role in Mesenchymal Differentiation Programs, in a Cell Fate Dependent Manner", PLoS ONE, vol. 3, Issue 11, e3707, 15 pages, (2008).

* cited by examiner

*Primary Examiner* — Robert S Landsman
*Assistant Examiner* — Bruce D. Hissong
(74) *Attorney, Agent, or Firm* — Vorys, Sater, Seymour and Pease LLP; Mih Suhn Koh

(57) ABSTRACT

Provided is a method for suppressing an adipose differentiation comprising administering to a subject in need thereof a PPAR-v neddylation inhibitor for inhibiting adipocyte differentiation and a method for screening an adipocyte differentiation inhibitor using PPAR-v neddylation associated with adipocyte differentiation. The inhibitor of a neddylation pathway of PPAR-v inhibits the differentiation from mesenchymal stem cells to mast cells, and thus can be effectively used to treat obesity, and particularly, can be also useful in the treatment of severe obesity which cannot be excepted to be treated by existing obesity treatment agents.

6 Claims, 23 Drawing Sheets
Specification includes a Sequence Listing.

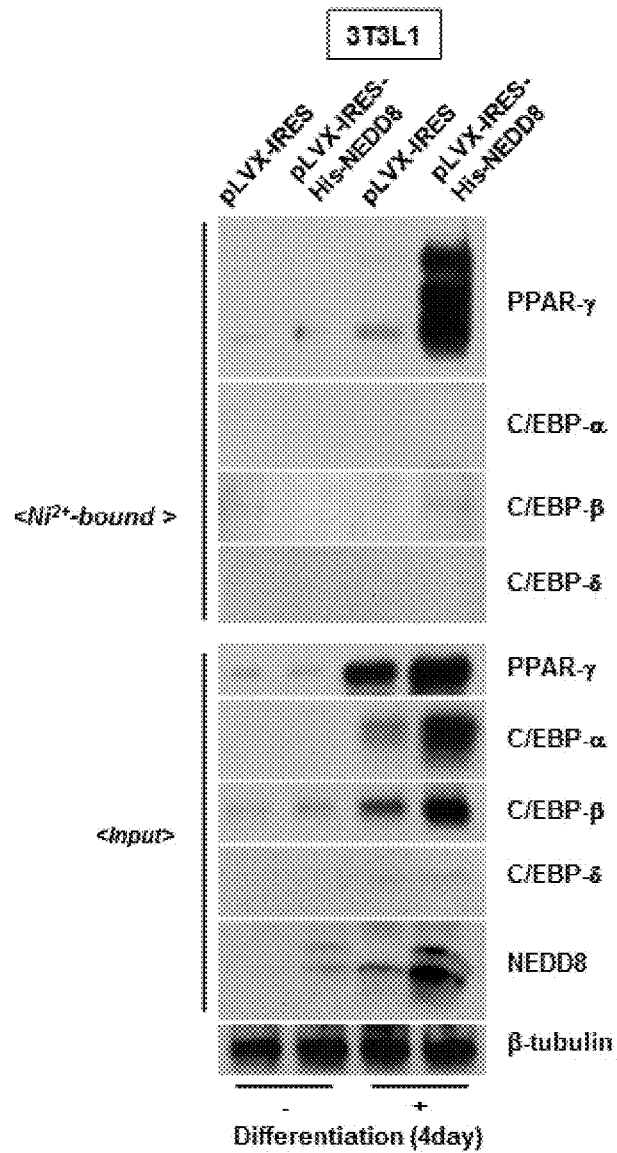

SEQUENCE LISTING

<160> NUMBER OF SEQ ID NOS: 26

<210> SEQ ID NO 1
<211> LENGTH: 25
<212> TYPE: RNA
<213> ORGANISM: Artificial Sequence
<220> FEATURE:
<223> OTHER INFORMATION: siRNA for NEDD8 from human

<400> SEQUENCE: 1
cagacaaggu ggagcgaauc aagga                                    25

<210> SEQ ID NO 2
<211> LENGTH: 27
<212> TYPE: RNA
<213> ORGANISM: Artificial Sequence
<220> FEATURE:
<223> OTHER INFORMATION: siRNA for NEDD8 from mouse

<400> SEQUENCE: 2
uccuugauuc gcuccaccuu gucugug                                  27

<210> SEQ ID NO 3
<211> LENGTH: 27
<212> TYPE: RNA
<213> ORGANISM: Artificial Sequence
<220> FEATURE:
<223> OTHER INFORMATION: siRNA for NEDD8 from mouse

<400> SEQUENCE: 3
uucacuuuaa uuagcaucuu cuuccca                                  27

<210> SEQ ID NO 4
<211> LENGTH: 27
<212> TYPE: RNA
<213> ORGANISM: Artificial Sequence
<220> FEATURE:
<223> OTHER INFORMATION: siRNA for APPBP1 from human

<400> SEQUENCE: 4
uauauauuug ccugaaucug caaucau                                  27

<210> SEQ ID NO 5
<211> LENGTH: 27
<212> TYPE: RNA
<213> ORGANISM: Artificial Sequence
<220> FEATURE:
<223> OTHER INFORMATION: siRNA for APPBP1 from mouse

<400> SEQUENCE: 5
gagcagauuc caaagcuucu uguccau                                  27

<210> SEQ ID NO 6
<211> LENGTH: 27
<212> TYPE: RNA
<213> ORGANISM: Artificial Sequence
<220> FEATURE:
<223> OTHER INFORMATION: siRNA for APPBP1 from mouse

<400> SEQUENCE: 6
agguaaauuu ccuugacccu ccuuggc                                  27

<210> SEQ ID NO 7
<211> LENGTH: 27
<212> TYPE: RNA
<213> ORGANISM: Artificial Sequence

```
<220> FEATURE:
<223> OTHER INFORMATION: siRNA for MDM2 from human

<400> SEQUENCE: 7
uuccugaagc ucuuguacaa gguccuu                                      27

<210> SEQ ID NO 8
<211> LENGTH: 25
<212> TYPE: RNA
<213> ORGANISM: Artificial Sequence
<220> FEATURE:
<223> OTHER INFORMATION: siRNA for MDM2 from mouse

<400> SEQUENCE: 8
gcaaugaucu acagaaauuu agugg                                        25

<210> SEQ ID NO 9
<211> LENGTH: 21
<212> TYPE: RNA
<213> ORGANISM: Artificial Sequence
<220> FEATURE:
<223> OTHER INFORMATION: siRNA for control

<400> SEQUENCE: 9
uugagcaauu cacguucauu u                                            21

<210> SEQ ID NO 10
<211> LENGTH: 56
<212> TYPE: RNA
<213> ORGANISM: Artificial Sequence
<220> FEATURE:
<223> OTHER INFORMATION: shRNA for mouse NEDD8-I

<400> SEQUENCE: 10
auuaaaaauu gauucgcucc accuugucuc ucgagagaca agguggagcg aaucaa       56

<210> SEQ ID NO 11
<211> LENGTH: 56
<212> TYPE: RNA
<213> ORGANISM: Artificial Sequence
<220> FEATURE:
<223> OTHER INFORMATION: shRNA for mouse NEDD8-II

<400> SEQUENCE: 11
auuaaaaaac uuuaauuagc aucuucuucc ucgaggaaga agaugcuaau uaaagu       56

<210> SEQ ID NO 12
<211> LENGTH: 56
<212> TYPE: RNA
<213> ORGANISM: Artificial Sequence
<220> FEATURE:
<223> OTHER INFORMATION: shRNA for mouse APPBP1-I

<400> SEQUENCE: 12
auuaaaaaca gauuccaaag cuucuugucc ucgaggacaa gaagcuuugg aaucug       56

<210> SEQ ID NO 13
<211> LENGTH: 57
<212> TYPE: RNA
<213> ORGANISM: Artificial Sequence
<220> FEATURE:
<223> OTHER INFORMATION: shRNA for mouse APPBP1- II

<400> SEQUENCE: 13
aauuaaaaau aaauuuccuu gacccuccuu cucgagaagg agggucaagg aaauuua      57
```

```
<210> SEQ ID NO 14
<211> LENGTH: 57
<212> TYPE: RNA
<213> ORGANISM: Artificial Sequence
<220> FEATURE:
<223> OTHER INFORMATION: Non-target (GFP)

<400> SEQUENCE: 14
aauuaaaaac gugaucuuca ccgacaagau cucgagaucu ugucggugaa gaucacg      57

<210> SEQ ID NO 15
<211> LENGTH: 20
<212> TYPE: DNA
<213> ORGANISM: Artificial Sequence
<220> FEATURE:
<223> OTHER INFORMATION: Forward Primer for mouse PPAR-gamma

<400> SEQUENCE: 15
agtggagacc gcccaggctt                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse Primer for mouse PPAR-gamma

<400> SEQUENCE: 16
cagttccagg gcctgcagca                                               20

<210> SEQ ID NO 17
<211> LENGTH: 24
<212> TYPE: DNA
<213> ORGANISM: Artificial Sequence
<220> FEATURE:
<223> OTHER INFORMATION: Forward Primer for mouse C/EBP-beta

<400> SEQUENCE: 17
accacgactt cctctccgac ctct                                          24

<210> SEQ ID NO 18
<211> LENGTH: 21
<212> TYPE: DNA
<213> ORGANISM: Artificial Sequence
<220> FEATURE:
<223> OTHER INFORMATION: Reverse Primer for mouse C/EBP-beta

<400> SEQUENCE: 18
cgtagtcggc cggcttcttg c                                             21

<210> SEQ ID NO 19
<211> LENGTH: 20
<212> TYPE: DNA
<213> ORGANISM: Artificial Sequence
<220> FEATURE:
<223> OTHER INFORMATION: Forward Primer for mouse CD36

<400> SEQUENCE: 19
gcttgcaact gtcagcacat                                               20

<210> SEQ ID NO 20
<211> LENGTH: 20
<212> TYPE: DNA
<213> ORGANISM: Artificial Sequence
<220> FEATURE:
<223> OTHER INFORMATION: Reverse Primer for mouse CD36
```

<400> SEQUENCE: 20
gccttgctgt agccaagaac                                            20

<210> SEQ ID NO 21
<211> LENGTH: 18
<212> TYPE: DNA
<213> ORGANISM: Artificial Sequence
<220> FEATURE:
<223> OTHER INFORMATION: Forward Primer for mouse FABP4

<400> SEQUENCE: 21
catggccaag cccaacat                                              18

<210> SEQ ID NO 22
<211> LENGTH: 20
<212> TYPE: DNA
<213> ORGANISM: Artificial Sequence
<220> FEATURE:
<223> OTHER INFORMATION: Reverse Primer for mouse FABP4

<400> SEQUENCE: 22
cgcccagttt gaaggaaatc                                            20

<210> SEQ ID NO 23
<211> LENGTH: 20
<212> TYPE: DNA
<213> ORGANISM: Artificial Sequence
<220> FEATURE:
<223> OTHER INFORMATION: Forward Primer for mouse NEDD8

<400> SEQUENCE: 23
aacccacaga caaggtggag                                            20

<210> SEQ ID NO 24
<211> LENGTH: 20
<212> TYPE: DNA
<213> ORGANISM: Artificial Sequence
<220> FEATURE:
<223> OTHER INFORMATION: Reverse Primer for mouse NEDD8

<400> SEQUENCE: 24
caaggaggta aacggaacca                                            20

<210> SEQ ID NO 25
<211> LENGTH: 19
<212> TYPE: DNA
<213> ORGANISM: Artificial Sequence
<220> FEATURE:
<223> OTHER INFORMATION: Forward Primer for mouse 18S

<400> SEQUENCE: 25
ttcgtattga gccgctaga                                             19

<210> SEQ ID NO 26
<211> LENGTH: 20
<212> TYPE: DNA
<213> ORGANISM: Artificial Sequence
<220> FEATURE:
<223> OTHER INFORMATION: Reverse Primer for mouse 18S

<400> SEQUENCE: 26
ctttcgctct ggtccgtctt                                            20

METHODS FOR SUPPRESSING ADIPOCYTE DIFFERENTIATION

CROSS-REFERENCE TO RELATED APPLICATIONS

The present application is a national stage application of International Patent Application No. PCT/KR2014/006527, filed Jul. 18, 2014, and claims the benefit of Korean Patent Application No. 2013-0084540, filed Jul. 18, 2013 in the Korean Intellectual Property Office, the disclosure of which are incorporated herein.

STATEMENT OF SEQUENCE LISTING

The Sequence Listing submitted in text format (.txt) filed on Jan. 15, 2016, named "SequenceListing.txt", created on Jan. 13, 2016 (4.88 KB), is incorporated herein by reference.

BACKGROUND OF THE INVENTION

Field of the Invention

The present disclosure is in the field of treating or preventing obesity.

Description of the Related Art

It has been suggested that major adult diseases including coronary arteriosclerosis, hypertension, hyperlipidemia or coronary heart disease and the like originate in overweight and obesity not only in adults but also in children.

Current treatment for obesity is based on two mechanisms. One is to regulate central nerve system and the other is to regulate digestive system. Drug belongs to the first classification is Lorcaserin (BELVIQ®) which is an agonist for serotonin 2C and Phentermine (FASTIN®, OSYMIA®) which releases noradrenalin. Orlistat (XENICAL®) inhibits the action of lipase released from stomach and pancreas. These drugs act by suppressing appetite and digestion or stimulating energy metabolism, which however, are associated with the side effects such as dizziness, headache, and trouble sleeping (Roger A. H, Trends in Neurosciences 2013;36(2):133-140).

Particularly in the case of severe obesity, the treatment is not effective with the conventional drugs because mast cells are continuously produced from adipose stem cells. Thus the gastrectomy is the only option in these patients, which however is not a satisfactory solution due to the side effects and high cost for the treatment in view of the efficacy. Thus there are needs to develop a new drug to treat obesity based on a fundamental approach which can prevent the generation of mast cells from adipocyte stem cells.

KR Patent No. 1232872 relates to a pharmaceutical composition comprising sphingosine-1-phospate or salts thereof for treating or preventing obesity and discloses treating obesity by suppressing the differentiation of mast cells in which sphingosine-1-phospate suppress the expression of PPAR-gamma (peroxisome proliferator activated receptor-gamma) and C/EBP (CCAT enhancer binding proteins) which are known to induce the differentiation of mast cells by activating or increasing the expression of sphingosine-1-phospate receptor 2.

There are needs to develop drugs for treating or preventing obesity based on the novel mechanism of suppressing adipocyte cell differentiation.

SUMMARY OF THE INVENTION

The present disclosure is to provide methods and composition to prevent or treat obesity based on a mechanism involved in the mast cell differentiation.

In one aspect of the present disclosure, there are provided composition comprising an inhibitor of neddylation of PPAR-v for suppressing the differentiation of an adipocyte. According to one embodiment, various inhibitors being able to suppress the neddylation of PPAR-v may be used for the present disclosure and include but are not limited to inhibitors of NEDD8, an E1 enzyme NAE, an E2 enzyme or E3 enzyme MDM2. According to other embodiment, such inhibitors are an agent that inhibits the expression or activity thereof and is selected from the group consisting of a small molecule, an antibody, an antisense oligonucleotide, a siRNA, a shRNA, a miRNA, and a polypeptide.

According to other embodiment, the NAE inhibitor is a MLN4924 or its salt or its derivative or its analogue such as hydrochloride salt, and the MDM2 inhibitor is a nutlin-3 or its salt or its derivative or its analogue.

According to other embodiment, the inhibitors are siRNAs or shRNAs wherein the NEDD8 inhibitor is a siRNA having a nucleic acid sequence selected from the group consisting of SEQ ID NOs: 1, 2 and 3 or a shRNA having a nucleic acid sequence selected from SEQ ID NOs: 10 or 11; the NAE inhibitor is a siRNA having a nucleic acid sequence selected from the group consisting of SEQ ID NOs: 4, 5 and 6; or a shRNA having a nucleic acid sequence selected from SEQ ID NOs: 12 or 13; and the MDM2 inhibitor is a siRNA having a nucleic acid sequence selected from SEQ ID NOs: 7 or 8.

The composition of the present disclosure can be advantageously used to treat or prevent obesity, particularly to treat or prevent obesity in which the conventional therapy has a limited efficacy such as severe or morbid obesity.

In other aspect of the present disclosure, there are provided a method of suppressing the differentiation of an adipocyte by inhibiting a neddylation pathway of PPAR-v. According to one embodiment, various inhibitors that inhibit the expression or activity the factors involved in the neddylation of PPAR-v may be used and include a small molecule, an antibody, an antisense oligonucleotide, a siRNA, a shRNA, a miRNA, and a polypeptide. According to other embodiment, the inhibitors are siRNAs or shRNAs wherein the NEDD8 inhibitor is a siRNA having a nucleic acid sequence selected from the group consisting of SEQ ID NOs: 1, 2 and 3 or a shRNA having a nucleic acid sequence selected from SEQ ID NOs: 10 or 11; the NAE inhibitor is a siRNA having a nucleic acid sequence selected from the group consisting of SEQ ID NOs: 4, 5 and 6; or a shRNA having a nucleic acid sequence selected from SEQ ID NOs: 12 or 13; and the MDM2 inhibitor is a siRNA having a nucleic acid sequence selected from SEQ ID NOs: 7 or 8.

In other aspect of the present disclosure, there are provided a screening an agent that suppresses the differentiation of adipocyte comprising the steps of: providing at least one of PPAR-v or a DNA binding domain of PPAR-v or a C-terminal ligand binding domain of PPAR-v, and at least one protein involved in the neddylation pathway of PPAR-v; contacting a test material which is expected to suppress the interaction between the at least one of PPAR-v or a DNA binding domain of PPAR-v or a C-terminal ligand binding domain of PPAR-v and the protein involved in the neddylation pathway of PPAR-v, or suppress the neddylation of the PPAR-v; detecting the interaction between the at least one of PPAR-v or DNA binding domain of PPAR-v or C-terminal ligand binding domain of PPAR-v and the protein involved in the neddylation pathway of PPAR-v or the neddylation of the PPAR-v; and selecting the test material as a candidate when the interaction between the at least one of PPAR-v or DNA binding domain of PPAR-v or C-terminal ligand binding domain of PPAR-v and the protein involved in the neddylation pathway of PPAR-v or the neddylation of the PPAR-v is reduced or not detected compared to a control which is not treated with a test material.

According to other embodiment, the protein involved in the neddylation pathway includes a NEDD8, an E1 enzyme NAE, an E2 enzyme or an enzyme MDM2. The proteins used in the present screening methods may be in various forms, particularly including a domain involved in the interaction and/or binding to PPAR-v or other proteins involved in the pathway. The proteins may be provided as an isolated form or as a cell expressing them. When the proteins are provided as cells expressing them, the cells endogenously express the proteins or the cells may be prepared by transient or stable transfection with genes encoding the protein. The cells which may be used for the present methods include a mesenchymal stem cell, a precursor of adipocyte or an adipocyte including for example HEK293, 3T3L1, 3T3, 3T3L1-F442A, 3T3-F442A, Ob17, PFC6, TA, 1246, or ST13 cells.

In other aspect of the present disclosure, there are provided a method of treating obesity comprising administering a therapeutically effective amount of an inhibitor of neddylation of PPAR-v or derivative thereof to a subject in need of treatment.

In other aspect of the present disclosure, there are provided a use of an inhibitor of neddylation of PPAR-v or derivative thereof to inhibit the differentiation of an adipocyte.

In other aspect of the present disclosure, there are provided a use of an inhibitor of neddylation of PPAR-v or derivative thereof to treat obesity Advantageous Effects The present disclosure is based on the discovery that the neddylations are involved in the adipocyte differentiation and provides agents or methods to treat or prevent obesity based on the new mechanism to suppress adipocyte differentiation. The compositions and methods of the present disclosure can be advantageously used to treat or prevent obesity by suppressing the differentiation of mesenchymal stem cells into adipocytes, particularly severe or morbid obesity in which the conventional therapies have not been effective.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1A is the results of Oil-red O staining to confirm the adipogenesis and the result of western blotting showing that the expression of PPAR-v, C/EBP-α, β, δ and NEDD8 are increased during the adipogenesis.

FIG. 1B is the results of western blotting and Oil-red O staining showing that the adipogenesis is suppressed when the NEDD8 expression was suppressed using siRNA and the E1 enzyme APPBP1 required for neddylation was suppressed.

FIG. 1C is the results of western blotting to examine the suppression of PPAR-v and Oil-red O staining to examine the adipogenesis in which the 3T3L1 cells were transfected with sh-control, sh-APPBP1-I, II, sh-NEDD8 I, or II using a viral vector to continuously suppress the expression of the corresponding gene.

FIG. 1D is the results of western blotting showing the decrease in the expression of PPAR-v and Oil-red O staining showing the effect on the adipogenesis in which the expression of NEDD8 was suppressed using siNEDD8 at 2 days before and after the differentiation was induced to test the possibility as therapeutics not only to suppress the differentiation into adipocyte also to affect the adipocytes generated.

FIG. 2A is the results of western blotting showing the effect of MLN4924 on the expression of PPAR-v, and Oil-red O staining showing the effect MLN4924 on the adipogenesis in which the cells were treated with MLN4924 at the concentration of 0.1 and 0.5 μM before and after the adipose differentiation was induced.

FIG. 2B is the results of RT-PCR showing the effect of MLN4921 on the expression of PPAR-v, C/EBP-β, CD36, and FABP4 at the mRNA level in which the cells were treated with 0.5 μM of MLN4924 and analyzed at 0. 2, 4, 6, and 8 days after the adipose differentiation was induced.

FIGS. 3A to 3E show that the expression of PPAR-v was stabilized by NEDD8.

FIG. 3A is the results of western blot showing that PPAR-v was stabilized by NEDD8 in HEK293 cells, which disappeared when neddylation deficient mutant NEDD8ΔGG was used (Left), and that PPAR-v was stabilized when it was expressed with NEDD8 (PPAR-v+NEDD8) followed by treatment with 100 μM of cycloheximide for 0, 3, 6, 9, 12 h (Right).

FIG. 3B is the results of $Ni^{2+}$ pull down assay and western blot to confirm the neddylation of PPAR-v and shows that the neddylation disappeared by NEDD8GG and SENP8.

FIG. 3C is the results of the $Ni^{2+}$ pull down assay and western blot performed on 3T3L1 cells stably transfected with viral vectors, pLVX-IRES, pLVX-IRES-His-NEDD8 4 days after the differentiation and shows that the endogenous PPAR-v was neddylated.

FIG. 3D is the results of western blot and shows that the neddylation of PPAR-v prevents the PPAR-v from being ubiquitinated and thus being degraded where the co-transfection of PPAR-v and Ub increased the ubiquitination of PPAR-v, which was reduced by the transfection of NEDD8.

FIG. 3E is the results of western blotting showing that the ubiquitination of PPAR-v was increased when the neddylation was inhibited using siNEDD8.

FIG. 4A is the results of western blotting showing that M and CT regions of PPAR-v were stabilized by NEDD8.

FIG. 4B is the result of Ni$^{2+}$ pull down assay and western blotting showing that the neddylation of PPAR-v occurred at M and CT region.

FIG. 4C is the result of Ni$^{2+}$ pull down assay and western blotting showing that the neddylation of PPAR-v at M, NT did not occurred with NEDD8ΔGG.

FIG. 5A is the results of immunoprecipitation to confirm the interaction PPAR-v and MDM2 in HEK293 cells using an antibody against MDM2.

FIG. 5B is the results of Ni$^{2+}$ pull down assay in HEK293 cells and western blotting showing that the neddylation of PPAR-v was increased when MDM2 was co-expressed.

FIG. 5C is the results of Oil-red O staining and western blotting in which 3T3L1 cells were transfected with each of siCon and siMDM2 at the concentration of 10, 20, or 50 nM and then induced to differentiate into adipocyte after 2 days, and shows that the adipose differentiation was suppressed in cells transfected with siMDM2.

FIG. 5D is the results of Oil-red O staining and western blotting in which the cells were treated with nutlin-3 at the concentration of 10 and 20 μM before and after the adipose differentiation was induced, and shows that the adipose differentiation was suppressed by the treatment.

FIG. 6A is the results of H&E staining and microscopic examination at 200× of the fat pads of the mice 5 days after the graft in which 3T3L1 cells stably expressing shCon or shNEDD8 in a viral vector were grafted into the subcutis of the chest, and shows that the adipose differentiation was observed in shCon group in contrast to shNEDD8 group in which the differentiation was inhibited.

FIG. 6B is the results of the same experiment as FIG. 6A except that 3T3-F442A cells were used and shows that the adipose differentiation was inhibited in shNEDD8 group.

FIG. 6C is the results of microscopic examination at 400× of the immunohistochemistry using anti-perilipin antibody to determine the lipid droplet and shows the lipid droplet was formed well in shCon group in contrast to shNEDD8 group in which the droplet formation was suppressed.

DETAILED DESCRIPTION OF THE EMBODIMENTS

Figure 1A:
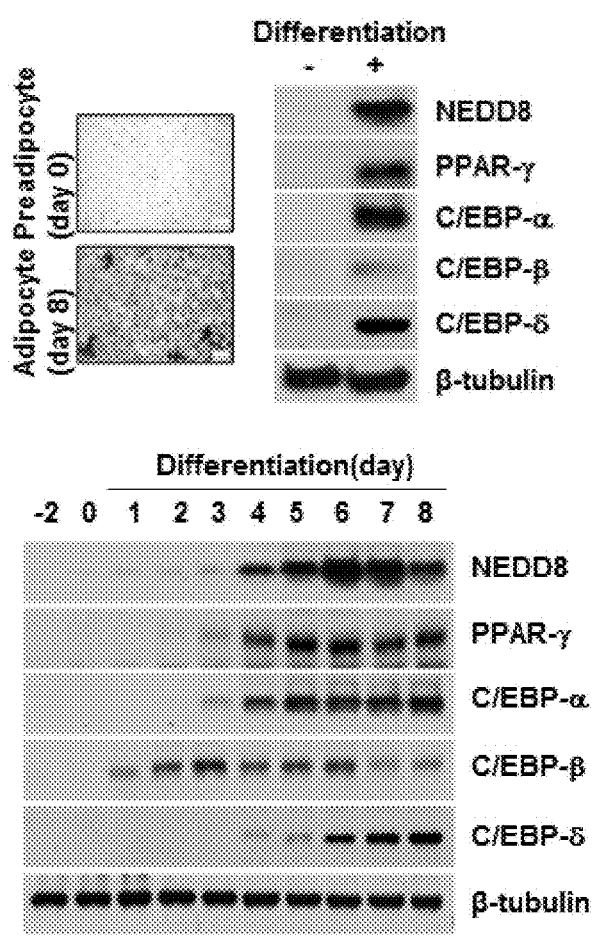
FIGS. 1A to D show that the expression of NEDD8 is increased in 3T3L1 cells during the adipogenesis.

The present disclosure is based on the discovery that PPAR-v (peroxisome proliferator activated receptor-gamma) is involved in the adipose differentiation by the neddylation thereof.

In one aspect, the present disclosure relates to a pharmaceutical composition comprising an inhibitor of the neddylation of PPAR-v for suppressing or inhibiting the adipose differentiation.

It has been shown in the art that many factors are involved in the differentiation of multipotent MSC (mesenchymal stem cells) into white adipocytes, and particularly C/EBP-beta and PPAR-gamma play an essential role in the adipose differentiation (Ma G. Cristancho, Nature Reviews Molecular Cell Biology 2011;12:722-734). However, how the factors are regulated, particularly in the regulation of the factors at the protein level is not known.

The neddylation is a type of protein modification process by which the ubiquitin-like protein NEDD8 is conjugated to its target proteins through E1 activating enzyme (NAE; a heterodimer of NAE1 and UBA3 subunit), E2 conjugating enzyme (Ubc12, UBE2M, and E3 ligase) (Gong et al. J. Biol. Chem. 2013; 274: 1203612042). The neddylation system is similar to UPS (ubiquitin-proteasome system) in which ubiquitin activating enzyme E1, ubiquitin conjugating enzyme E2 (UBC) and ubiquitin-protein isopeptide ligase E3 are involved (Hershko, A. Cell Death Differ. 2005; 12: 1191-1197). Nedd8 (Neural precursor cell-Expressed Developmental Downregulation 8) is a protein similar to ubiquitin of about 9 kDa in size having 81 amino acids and known to be involved in the proliferation, viability and development of neural precursor cells in which Nedd8 is down regulated during the brain development in mice. However its role in the adipose differentiation is not known.

NAE is the enzyme previously known to be involved in the neddylation and has also been known to play an essential role in the growth of cancer cells by regulating the activity of cullin-RING (really interesting new gene) subtype of ubiquitin ligase (Pan, Z. Q. et al., Oncogene 2004; 23: 1985-1997). However its role in the adipose differentiation is not known.

In the present disclosure, it has been found that the neddylation of PPAR-v induces the adipose differentiation. Thus the suppression or inhibition of adipose differentiation can be achieved through inhibition of the enzymes involved in the neddylation of PPAR-v pathway.

In this context, various synthetic or natural inhibitors that are able to suppress any one of the proteins involved in the neddylation of PPAR-v as described herein are encompassed in the present disclosure. For example, inhibitors of NEDD8, E1 enzyme NAE, E2 enzyme and E3 enzyme MDM2 ligase are included in the present disclosure. In one embodiment, the inhibitors which may be utilized in the present disclosure can be selected in screening methods as described in hereinafter.

In the present compositions and methods, various synthetic or natural agents or materials that can inhibit the factors such as NEDD8, NAE, E2 and/or MDM2 involved in the neddylation of PPAR-v pathway can be employed. The agent or materials that can inhibit the expression or activity of NEDD8, NAE, E2 and/or MDM2 at the transcriptional and/or translational level include, but are not limited to, for example small molecules, proteins including antibodies and polypeptides, and nucleic acid molecules including such as RNA and DNA for example antisense oligonucleotides, siRNA, shRNA or miRNA, or any combinations thereof.

The term "expression" as used herein refers to a process or steps involved in the process by which the genes are expressed into proteins, including the transcription of the genes into mRNAs, and the translation of mRNAs into proteins.

The term "activation" as used herein refers to a biological process by which the expressed protein of interest can function as expected in cells.

In one embodiment, the inhibitors which may be comprised in the present composition or used for the present methods include inhibitors of NEDD8 activating enzyme (NAE) for example MLN4924 or its enantiomers, or its derivatives or its analogues. MLN4924 is an agent which is known for its therapeutic effects on solid cancer and blood cancer and is similar to adenosine 5'-monophosphate (AMP) (Haas, A. L. et al., J. Biol. Chem. 1982; 257:10329-10337; Bohnsack, R. N. et al., J. Biol. Chem. 2003; 278: 26823-26830). Its apoptotic effects on cancer cells are also known (Soucy, T. A. et al., Nature 2009; 458:732-737). However, its function or activity in relation to the suppression of adipose differentiation is not known.

In other embodiment, the inhibitors which may be comprised in the present composition or used for the present methods include inhibitors of E3 ligase, i.e., MDM2 inhibitors. It was found in the present disclosure that E3 ligases involved in the neddylation of PPAR-v is indeed MDM-2, and thus various materials or agents which are able to inhibit the expression and/or function and/or activity of MDM-2 may be advantageously used for the present purpose. For example, nutlin-1, nutlin-2 and nutlin-3, nutlin-3a, nutlin-3b or its enantiomers, or its derivatives or its analogues are encompassed in the present disclosure. In one embodiment, nutlin-3 is particularly used. Nutlin-3 (4-[4,5-Bis(4-chlorophenyl)-2-(2-isopropoxy-4-methoxy-phenyl)-4,5-dihydro-imidazole-1-carbonyl]-piperazin-2-one) is an analogue of cis-imidazoline and known to inhibit the interaction between p53 and MDM-2 (Vassilev L T, et al. Science 2004;303 (5659): 844-848). But its role in the adipose differentiation is not known.

In other embodiment, inhibitors of the neddylation of PPAR-v which may be used in the present disclosure are antibodies which specifically recognize and thus inhibit, suppress or interfere with the activity and/or function of at least one of the factors involved in the neddylation pathway. The term antibody as used herein includes intact antibodies, fragments thereof, antigen binding fragments thereof, or any functional equivalents thereof. Also the antibody included are IgG, IgM, IgD, IgE, IgA or IgY type, or IgG1, IgG2, IgG3, IgG4, IgA1 or IgA2 class or subclass thereof. The antibodies which may be employed for the present discourse include monoclonal antibodies, polyclonal antibodies, chimeric antibodies, single chain antibodies, bispecific antibodies, humanized or simianized antibodies, and active fragments thereof or antibody mimetics.

In other embodiment, inhibitors of the neddylation of PPAR-v which may be employed in the present disclosure are polypeptides which are able to inhibit, suppress or prevent the activity, expression and/or function/mechanism of the factors involved in the neddylation of PPAR-v pathway. The term polypeptide as used herein refers to a synthetic or natural polymer of amino acids of any length and includes peptides and oligopeptides as long as they exert the function according to the present disclosure. In one embodiment, the polypeptides which may be used for the present disclosure include ones comprising all or part of the region contacting/interacting with the factors involved in the neddylation of PPAR-v pathway or the region adjacent thereto. The polypeptides which may be used in the present disclosure can compete with MDM-2 in cells to inhibit the normal function of MDM-2 working as a competitive inhibitor. The polypeptides include synthetic, natural or artificially modified ones such as glycosylated, acetylated, or phosphorylated polypeptides and the like.

In still other embodiment, inhibitors of the neddylation of PPAR-v which may be employed in the present disclosure are nucleic acid molecules which are able to suppress the expression of NEDD8, NAE, E2 and/or MDM-2 such as for example siRNA (small interfering RNA), shRNA (small hairpin RNA) or miRNA (microRNA). The siRNAs, shRNAs and miRNAs are RNA molecules silencing the target gene expression by an interference function in which small interfering RNAs (siRNAs) bind specifically to a sequence in a target transcript and form a RISC (RNA Induced Silencing Complex) thus blocking the translation of the target gene into proteins. The siRNAs, shRNAs or miRNAs of the present disclosure have a sequence significantly complementary to its target. The significant complementarity means a sequence complementarity of at least about 70%, at least about 80%, at least about 90% or at least about 100% to at least 15 continuous bases in targets. In one embodiment of the present disclosure, siRNA having a sequence represented by SEQ ID NOs: 1, 2 or 3, or shRNA having a sequence represented by SEQ ID NOs: 10 or 11 is used as a NEDD8 inhibitor. In other embodiment of the present disclosure, siRNA having a sequence represented by SEQ ID NOs: 7 or 8 is used as a MDM2 inhibitor without being limited thereto. Antisense oligonucleotides, siRNAs, shRNAs and/or miRNAs, or their biological equivalents, derivatives and analogues of various origins and types may be used as long as they are able to target and silence the genes related to the neddylation of PPAR-γ of the present disclosure by binding thereto. Antisense oligonucleotides are a short synthetic nucleotide sequence known in the art which bind to a target mRNA thus reducing/suppressing the protein expression. Antisense RNAs may have various lengths depending on the types of target and/or of the delivery methods employed and are for example about 6, 8, or 10 to 40, 60 or 100 bases in length.

The compositions and methods of the present disclosure can be advantageously used to suppress or inhibit the adipose differentiation, particularly to treat or prevent morbid obesity.

In this perspective, the present disclosure relates to a method to treat or prevent obesity comprising administering to a subject, for example a mammal, particularly a human in need of such treatment a therapeutically effective amount of an inhibitor of the neddylation of PPAR-v. The therapeutically effective amount in relation to treatment/prevention of obesity refers to an amount of the material, agent or pharmaceutical composition described herein that is sufficient to effect the intended therapeutic efficacy for example alleviating or reducing obesity or any symptoms associated therewith.

The term "obesity" as used herein refers to a medical condition or disease in which adipose tissue (body fat) is systemically accumulated as a result of, for example, energy intake that is higher than energy expenditure over a period of time. Embodied in the present disclosure are obesity classified according to body mass index (BMI) of WHO which is defined as a measure of a person's body weight divided by the square of its height in meters and is classified as follows: a BMI value of 23 to 24.99 (highest normal), 25.0 to 29.99 (overweight), ≥30 (obese), ≥40 (morbid obese) and ≥40 (super obese). Also embodied in the present disclosure are obesity which include endocrine obese (endocrine abnormalities or brain diseases), primary obese (excess intake of calories), hyperplastic obese (due to the creation of new fat cells), and hypertrophic obese (due to the expansion of existing fat cells); upper body obese and lower body obese; or visceral obese and subcutaneous obese.

As used herein, the terms "treat," "treatment," and "treating" refer to alleviating, abating or ameliorating at least one symptoms of obesity, and/or reducing severity, progression and/or duration thereof, and/or preventing additional symptoms, and include prophylactic and/or therapeutic measures. An ordinary person in the related art is able to determine the degree or extent of treating, alleviating, abating or ameliorating based on the information disclosed in such as, for example, Korean Academy of Medical Sciences.

As used herein, the terms "prevention" or "preventing" refer to delay or suppression of onset of obesity or symptoms associated with the disorder by the administration of the present composition or materials. It is evident to an ordinary person in the art that the present methods or compositions with anti-obesity effect are able to prevent when it is taken or used before the onset of obesity.

The present composition or method may further comprise one or more of additional active ingredient with activities identical or similar to the inhibitors as described above and/or agents that enhance the bioavailability of the present inhibitors in vivo.

Also encompassed are the combined use of the present inhibitors with other therapies to treat and/or prevent obesity, which includes surgery, drug therapy and use of biological response modifiers.

The present composition may further includes one or more pharmaceutically or physiologically acceptable carriers.

The term "carriers" as used herein include but do not limited to, saline, sterilized water, Ringer's solution, buffered saline, buffers such as phosphate, citrates and other organic acids, antioxidant such as ascorbic acids, low molecular weight (about less than 10 amino acids) polypeptides, proteins such as serum albumin, gelatin or immunoglobulin; hydrophilic polymer such as polyvinylpyrrolidone, amino acids such as glycine, glutamine, asparagine, arginine or lysine, carbohydrates such as monosaccharides, disaccharides, and glucose, mannose or dextrin, chelating agents such as EDTA, sugar alcohols such as mannitol or sorbitol, counter ions for salt formation such as Sodium, and/or non-ionic surfactant such as Tween, polyethylene glycol (PEG) and PLURONICS®.

If desired, the composition may further comprise antioxidants, buffers, antibacterial agents, and other additives known in the art to prepare pharmaceutical compositions. The present composition may be formulated into injectable formulations or oral formulations such as capsules, granules, or tablets by methods known in the art using one or more of diluents, dispersing agents, surfactants, binders and lubricants. Also encompassed for the present invention is a target specific composition combined with an antibody or other ligands that specifically recognize a molecule present on a target tissue or organ of interest. Further latest edition of Remington's Pharmaceutical Science (Mack Publishing Company, Easton Pa., USA) may be referred for the preparation and formulation of pharmaceutical composition.

The present composition can be administered by various routes known in the art such as oral or parenteral delivery for example intravenous, subcutaneous, or intraperitoneal injections or delivery through patch, nasal or respiratory patches. In one embodiment, injections are preferred.

Desirable or optimal dosage may vary among patients depending on various factors such as body weight, age, sex, general condition of health, diet, severity of diseases, and excretion rate. Where siRNA, miRNA, antisense oligonucleotides, shRNA and proteins including polypeptides are used, parenteral deliveries are preferred. The typical unit dosage includes but does not limit to for example about 0.01 mg to 100 mg a day. Typical daily dosage ranges from about 1 μg to 10 g and may be administered one or multiple times a day.

In other aspect, the present disclosure relates to an in vivo or in vitro method to inhibit adipose differentiation via suppressing the neddylation of PPAR-v pathway. Inhibitors to suppress the neddylation of PPAR-v pathway which may be included in the present methods are as described above and include inhibitors that are able to inhibit the expression or activity of at least one of NEDD8, E1 enzyme NAE, E2 enzyme or E3 enzyme MDM2.

The present disclosure is based on the discovery that the neddylation of PPAR-v is essential for adipose differentiation. Thus any agents which are able to suppress the interaction of PPAR-v with the factors involved in the neddylation of PPAR-v may be screened and selected as potential therapeutic agents for treating obesity.

In this perspective, the present disclosure relates to a method for screening a compound with a potential to inhibit adipose differentiation, which is based on the inhibition of the neddylation of PPAR-v pathway.

In one embodiment, the present method comprises a step of providing at least one of PPAR-v or DNA binding region of PPAR-v or C-terminal ligand binding region of PPAR-v and at least one of the factors involved in the neddylation of PPAR-v; a step of contacting the proteins as above step with a test substance which is expected to inhibit the interaction of the PPAR-v or DNA binding region of PPAR-v or C-terminal ligand binding region of PPAR-v with the factors, and/or the neddylation of PPAR-v; and a step of detecting the interaction between at least one of the PPAR-v or DNA binding region of PPAR-v or C-terminal ligand binding region of PPAR-v and at least one of the factors, or the neddylation of PPAR-v, in which a test substance is selected as a candidate when the candidate decreases the interaction between at least one of the PPAR-v or DNA binding region of PPAR-v or C-terminal ligand binding region of PPAR-v and at least one of the factors involved in the neddylation of PPAR-v, or the neddylation of PPAR-v or when no such activity is detected compared to a control which is not contacted with a test substance.

The partial or entire length of PPAR-v proteins are employed in the present disclosure. For example entire length of PPAR-v protein, the regions or domains of PPAR-v protein contacting/interacting with the factors involved in the neddylation and/or the neddylation region are included. PPAR-v comprises N-terminal trans-activating domain (AF1, NT amino acid residues 1-140), highly conserved DNA binding domain (DBD, M; amino acid residues 141-281) and C-terminal ligand binding domain (LBD, CT amino acid residues 282-505) (Maryam Ahmadian, Nature Medicine 2013;9:557566). The protein and nucleotide sequence of PPAR-v are known in the art. For example, human sequence is disclosed as NCBI Reference sequence (NP_035276.2). In one embodiment of the present disclosure, the neddylation region M and/or CT region, or various length of PPAR-v comprising such region is used.

The sequences of NAE, E2 and MDM-2 involved in the neddylation of and/or the interaction with PPAR-v are known in the art as NAE NP_003896.1, E2 UBC12 or UBE2M NP_003960.1 and MDM-2 NP_002383.2. Proteins of various lengths including entire or partial length, particularly the region interacting with PPAR-v are used.

Proteins of various origins may also be used in the present methods according to the specific embodiments employed. For example, a protein originated from a mammal, particularly a human or a mouse may be used. Also proteins with a same origin for example a human origin may have a different sequence depending on the individuals, particular regions or environment and the like, which are also encompassed in the present methods. Further proteins and any functionally equivalent thereof may also be used for the present disclosure. Also proteins with some modifications in the sequence such as deletion, substitution, and addition may be used.

The protein of the present disclosure may be provided as an isolated form or as a cell or cell line expressing such proteins endogenously or exogenously by transfecting (stable or transient) the cells with an appropriate plasmid.

The protein of the present disclosure may be prepared by methods known in the art. In one embodiment, recombinant technologies are used, in which for example a plasmid comprising a gene encoding the present protein is introduced into prokaryotic or eukaryotic cells such as insect cells or mammalian cells for overexpression. The proteins are then extracted and purified before use. Plasmids for cloning are known in the art and include but is not limited to vectors such as pcDNA™ (Clontech Laboratories, USA).

Further Nucleic acids encoding a protein used for the present screening method may be transcribed and/or translated in vitro and processed further before being used for the present methods. In one embodiment, the in vitro translated proteins may be further processed by centrifugation to remove the cell debris followed by purification by precipitation, dialysis, and column chromatography, the example of which includes ion exchange chromatography, gel-permeation chromatography, HPLC (high performance liquid chromatography), reverse phase HPLC, preparative SDS-PAGE, affinity column chromatography. The affinity column chromatography may be prepared using antibody against a protein of interest.

In other embodiment, the present proteins are provided as a cell that endogenously or exogenously expressing the protein. For example, mammalian cells expressing a protein of interest endogenously or exogenously by transient or stable transfection such as stem cells which is potential to differentiate into adipocytes, preadipocytes and adipocytes are included in the present disclosure. Examples of such cells include but are not limited to HEK293 (Human embryonic kidney): 3T3L1, 3T3-F442A, TA or 3T3L1/3T3 F442A originated from white fat tissue/embryonic fibroblast; Ob17 originated from white fat tissue/testis fat cells, PFC6 originated from white fat tissue/stromal-vascular fraction of epididymis fat, 1246 cells originated from white fat tissue/teratocarcinoma, ST13 cells originated from white fat tissues carcinoid (Klein et al. BioEssays 2002;24(4):382388). For example, the cells such as HEK293 are transfected with a plasmid harboring full or partial length of PPAR-v gene and a plasmid harboring MDM-2 gene, or a plasmid harboring both of such genes. Then the cells are treated with a test substance and the treated cells are compared with control cells which are not treated with the test substance. The test substance may be identified as a candidate for suppressing the differentiation of adipocytes and thus for treating or preventing obesity when it reduces or suppress the interaction of the proteins involved as compared to the control.

The effect of a test substance on the protein-protein interaction may be detected by a variety of methods known in the art. The example includes but is not limited to yeast two hybrid method, confocal microscopy, co-immunoprecipitation, surface plasmon resonance (SPR) and spectroscopy. Reference may be found in Berggard et al., (2007) "Methods for the detection and analysis of protein-protein interactions", PROTEOMICS Vol7: pp 2833-2842.

The term interaction as used herein refers to contacting or binding among the same or different proteins, and includes an interaction through a covalent or non-covalent binding. The substances that induce or cause a change and/or decrease in the interaction are selected as a candidate for treating or preventing obesity or for suppressing adipocyte differentiation.

The present disclosure is based on the discovery that the neddylation of PPAR-v is involved in the adipocyte differentiation. Thus in this perspective, screening of the candidates according to the present disclosure may also be performed by detecting the neddylation of PPAR-v. Methods for detecting the neddylation of PPAR-v are known in the art and include but are not limited to methods described in the present Examples.

The amount of proteins, the types of cells and the amount and types of test substances employed in the present methods may vary depending on the particular process, test substances employed, which can be appropriately selected by a skilled person in the art without undue burden. The substances that cause no neddylation or reduction/suppression/inhibition in the neddylation are selected as a candidate compared with a control which is not treated with a test substance. The level of reduction/suppression/inhibition means the level not more than about 99%, about 95% about 90%, about 85%, about 80%, about 75%, about 70%, about 65%, about 60%, about 55%, about 50%, about 45%, about 40%, about 30%, about 20% in comparison to that of a negative control, but is not limited thereto.

The terms "test substance" "test agents" or "test compound" as used herein refer generally to a material that is expected to decrease, reduce, suppress or inhibit the neddylation of PPAR-v, which includes small molecules, high molecular weight molecules, mixture of compounds such as natural extracts or cell or tissue culture products, biological material such as proteins, antibodies, peptides, DNA, RNA, antisense oligonucleotides, RNAi, aptamer, RNAzymes and DNAzymes, or glucose and lipids, but is not limited thereto. The test substances may be polypeptides having amino acid residues of below 20, particularly 6, 10, 12, 20 aa or above 20 such as 50 aa. These materials are obtained from synthetic or natural compound libraries and the methods to obtain or construct libraries are known in the art. For example, synthetic chemical library may be obtained from Maybridge Chemical Co. (UK), Comgenex (USA), Brandon Associates (USA), Microsource (USA) and Sigma-Aldrich (USA). The chemical library of natural origin may be obtained from Pan Laboratories (USA) and MycoSearch (USA). Further test substances may be obtained by various combinatorial library construction methods known in the art including for example, biological libraries, spatially addressable parallel solid phase or solution phase libraries, synthetic libraries that require deconvolution, "1-bead 1-compound" libraries, synthetic libraries that require that use affinity chromatography. Various library preparation methods may be found in DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994, Houghten, R. A. et al. 1991 Nature 354:84-86 and the e like.

In one embodiment, small molecules are used to identify agents useful for treating and/or preventing obesity or symptoms associated therewith or for suppressing the neddylation. For example small molecules with molecular weight of about less than 1,000 Da such as 400 Da, 600 Da, or 800 Da. If desired, small molecules may form part of a library, the total number of small molecules included therein may vary from dozens to millions. Test substance of a library may be composed of peptides, peptoides, circular or liner oligomeric compounds, template based compounds such as benzodiazepine, hydantoin, biaryls, carbocyclic and polycyclic compounds such as naphthalene, phenothiazine, acridine, steroids and the like, carbohydrate and amino acid derivatives, dihydropyridine, benzhydryl and heterocyclic compounds such as triazine, indole, thiazolidine and the like, but does not limited thereto.

Also employed for the present methods are biologics. Biologics generally refer to cells or biomolecules such as proteins including antibodies, peptides or other proteins found in plasma, nucleic acids such as polynucleotides, carbohydrates, lipids or any materials produced in vivo or in vitro by biological systems such as cell culture system. For the purpose of the present invention, biomolecules may be used alone or in combination with others.

The present disclosure is further explained in more detail with reference to the following examples. These examples, however, should not be interpreted as limiting the scope of the present invention in any manner.

EXAMPLES

Materials and Methods Used in the Present Examples are as Below.

Antibodies

Antibodies against PPAR-v(sc-1796, sc-1984), C/EBP- (sc-14AA), C/EBP-α (sc-C-19), C/EBP-β (M-17), β-tubulin (H-235), MDM2 (sc-965), Ub (sc-9133) antibodies was obtained from Santa Cruz Biotechnology (Santa Cruz, Calif., USA), NEDD8 (2745), perilipin (9349) were obtained from Cell signaling Technology (Beverly, Mass.). Anti-HA was obtained from Roche Applied Science (Penzberg, Germany).

Reagents

3-Isobutyl-1-methylxanthine (IBMX, I5879), dexamethasone (D4902), insulin (I1507), cycloheximide (C1988), HA-affinity beads (E6779), D-glucose (G7021), human insulin (I9278), Oil Red O(O0624) and EZview™ Red anti-HA affinity gel (E6779) were obtained from Sigma-Aldrich (St. Louis, Mo.). Nutlin-3 (10004372) was obtained from Cayman Chemical Company (Ann Arbor, Mich.). MG132 was obtained from ENZO Life Sciences (Farmingdale, N.Y.). Ni-NTA agarose beads were obtained from Qiagen (Hilden, Germany). MLN4924 was synthesized, as previously described (J Org Chem. 2011;76(9):3557-61.).37 Bovine serum, fetal bovine serum (FBS) and Dulbecco's modified Eagle's medium (DMEM) were obtained from Thermo Fisher Scientific (Waltham, Mass.).

Cell Culture and Adipocyte Differentiation

HEK293 (human embryonic kidney) cells were obtained from the American Type Culture Collection (Manassas, Va.). 3T3-L1 and 3T3-F442A preadipocytes were kindly given by Dr. Jae-Woo Kim (Yonsei University, Seoul, Korea). Cells were cultured in DMEM supplemented with 10% fetal bovine serum (FBS). Differentiation of 3T3-L1 cells was induced with 1 μM dexamethasone, 500 μM 3-isobutyl-a-methylxanthine, and 5 μg/ml of insulin (DMI), which is designated DMI. From 2 to 8 days after DMI treatment, cells were maintained in DMEM containing 10% FBS and 1 μg/ml of insulin and the medium was changed every other day. Adipocyte differentiation of hADSCs was induced with DMI and 200 μM indomethacin in α-MEM supplemented with 10% FBS. Cells were incubated in 5% CO2 and 20% O2 at 37° C.

Plasmids, siRNAs, shRNAs, and Transfection

The vectors expressing HA-PPAR-v and HA-C/EBP-β were kindly given by Dr. Kyung-Soo Park (Seoul National University, Seoul, South Korea). NEDD8 cDNA obtained by reverse transcription-PCR (RT-PCR) was cloned into His6-tagged pcDNA3. The NEDD8-ΔGG mutant was generated by site-directed mutagenesis (Ryu et al. J. Biol. Chem. 2011;274:1203612042). The mutant has a Gly-75 and a deletion in carboxy terminus and cannot form a conjugate with a target.

HA-Ub, HA-PPAR-v-NT, HA-PPAR-v-M, HA-PPAR-v-CT expression vectors were obtained by cloning a corresponding fragment amplified by PCR into HA-tagged pcDNA3 (Clontech Laboratories, Mountain View, Calif.). PCR-amplified cDNAs of human MDM2 and SENP8 were inserted into pcDNA (Clontech), Myc-tagged pcDNA (Clontech), respectively. Flag/SBP-MDM2 was inserted into SFB-pIRES2-EGFP vector (Clontech Laboratories), MDM2 (NP_002383.2) was inserted into pIRES2-EGFP vector by a blunt end ligation. The siRNA used for the present Examples are as in Table 1 and were obtained from IDT Integrated DNA Technologies Inc. (USA).

TABLE 1

| Name | Gene Accession No. | Sequence | SEQ ID NOs |
|---|---|---|---|
| siNEDD8 | human (NM_006156.2) | 5'-CAGACAAGGUGGAGCGAAUCAAGGA-3' | SEQ ID NO: 1 |
| siNEDD8-I | mouse (NM_008683.3) | 5'-UCCUUGAUUCGCUCCACCUUGUCUGUG-3', | SEQ ID NO: 2 |
| siNEDD8-II | mouse (NM_008683.3) | 5'-UUCACUUUAAUUAGCAUCUUCUUCCCA-3' | SEQ ID NO: 3 |
| siAPPBP1 | human (NM_003905.3) | 5'-UAUAUAUUUGCCUGAAUCUGCAAUCAU-3' | SEQ ID NO: 4 |
| siAPPBP1-I | mouse (NM_144931.3) | 5'-GAGCAGAUUCCAAAGCUUCUUGUCCAU-3' | SEQ ID NO: 5 |
| siAPPBP1-II | mouse (NM_144931.3) | 5'-AGGUAAAUUUCCUUGACCCUCCUUGGC-3' | SEQ ID NO: 6 |
| siMDM2 | human (NM_002392.5) | 5'-UUCCUGAAGCUCUUGUACAAGGUCCUU-3' | SEQ ID NO: 7 |
| siMDM2 | mouse (NM_010786.3) | 5'-GCAAUGAUCUACAGAAAUUUAGUGG-3' | SEQ ID NO: 8 |
| siControl | | 5'-UUGAGCAAUUCACGUUCAUUU-3' | SEQ ID NO: 9 |

In Table 1, the second column from the left indicates gene number from which each siRNA was originated. The constructed plasmids and siRNAs were transfected into cells using Lipofectamine® 2000 Transfection Reagent (Invitrogen) according to the manufacturer's instruction.

RNA Preparation and Quantitative RT-PCR

Total RNAs were isolated from cultured cells using TRIzol® (Invitrogen). The EasyScript™ cDNA Synthesis Kit (Applied Biological Materials Inc., Richmond, Canada) was used to synthesize cDNAs. The level of each cDNA was relatively quantified by being divided by the 18S rRNA level in the corresponding sample. The sequences of qPCR primers are listed in Table 2.

TABLE 2

| Name | Sequences | SEQ ID NOs |
|---|---|---|
| PPAR-γ mouse | For 5'- AGTGGAGACCGCCCAGGCTT -3'<br>Rev 5'- CAGTTCCAGGGCCTGCAGCA-3' | SEQ ID NO: 15<br>SEQ ID NO: 16 |
| C/EBP-β mouse | For 5'- ACCACGACTTCCTCTCCGACCTCT -3'<br>Rev 5'- CGTAGTCGGCCGGCTTCTTGC -3' | SEQ ID NO: 17<br>SEQ ID NO: 18 |
| CD36 mouse | For 5'- GCTTGCAACTGTCAGCACAT - 3'<br>Rev 5'- GCCTTGCTGTAGCCAAGAAC- 3' | SEQ ID NO: 19<br>SEQ ID NO: 20 |
| FABP4 mouse | For 5'- CATGGCCAAGCCCAACAT -3'<br>Rev 5'- CGCCCAGTTTGAAGGAAATC-3' | SEQ ID NO: 2<br>SEQ ID NO: 22 |
| NEDD8 mouse | For 5'-AACCCACAGACAAGGTGGAG -3'<br>Rev 5'-CAAGGAGGTAAACGGAACCA -3' | SEQ ID NO: 23<br>SEQ ID NO: 24 |
| 18S mouse | For 5'- TTCGTATTGAGCCGCTAGA -3'<br>Rev 5'- CTTTCGCTCTGGTCCGTCTT -3' | SEQ ID NO: 25<br>SEQ ID NO: 26 |

Western Blotting and Immunoprecipitation

Proteins in cell lysates were electrophoresed on SDS-polyacrylamide gels and transferred to Immobilon-P membranes (Millipore, Billerica, Mass.). Membranes were pre-incubated with 5% skim milk in TTBS (Tris-buffered saline containing 0.1% Tween 20) for 30 min and incubated overnight with primary antibody diluted 1:500 to 1:3000 in the TTBS. The membranes were further incubated with a horseradish peroxidase conjugated secondary antibody for 1 h and visualized using Pierce ECL Plus western blotting substrate according to the manufacturer's instruction (Thermo Fisher Scientific, Waltham, Mass.).

To precipitate HA-tagged proteins, transfected cells were lysed in a buffer containing 5 mM EDTA, 50 mM Tris-Cl, 100 mM NaCl, 0.1% NP-40, and the protease inhibitor cocktail (Sigma-Aldrich). Cell lysates (1 mg proteins) were incubated with EZview™ anti-HA affinity beads sequentially incubated with a primary antibody (10 μg/mL) and protein A/G-Sepharose beads (GE Healthcare, Uppsala, Sweden) at 4° C. for 4 h. Pull down proteins were eluted in a 2×SDS denaturing buffer and subjected to Western blotting as described above. For HA-bead immunoprecipitation, 1 mg of protein was incubated with 10 ul of HA-bead at 4° C. for 4 h and washed. Then proteins were eluted in a 2×SDS denaturing buffer and electrophoresed in a SDS-PAGE gel and subjected to Western blotting as described above.

Identification of $His_6$-tagged NEDD8 Conjugation

Each of $His_6$-tagged NEDD8 or NEDD8ΔGG plasmid was transfected and divided into two dishes. One dish was used for western blot to confirm the protein expression and the other dish was used for pull-down assay.

For the pull-down assay, the cells were lysed in a denaturing buffer comprising 6M guanidine hydrochloride, 0.1M $Na_2HPO_4/NaH_2PO_4$, 0.01M Tris-Cl (pH8), 10 mM imidazole, 10 mM β-mercaptoethanol. The lysates were incubated with $Ni^{2+}$-NTA-agarose bead (Qiagen) at RT for 4 h, which was then washed with a first washing buffer [pH8, 8M urea, 0.1M $Na_2HPO_4/NaH_2PO_4$, 0.01M Tris-Cl (pH8), 20 mM imidazole, 10 mM β-mercaptoethanol] and a second wash buffer [pH6.3, 8M urea, 0.1M $Na_2HPO_4/NaH_2PO_4$, 0.01M Tris-Cl (pH8), 20 mM imidazole, 10 mM β-mercaptoethanol, 0.2%, 0.1% of Triton®-X100]. Then His-tagged proteins were eluted in a 2×SDS denaturing buffer and subjected to a western blot.

Oil-red O Staining

Adipocytes were fixed with 3.7% of formalin and stained with 0.3% Oil-red-O solution (Sigma-Aldrich) dissolved in isopropanol. 0.5% Oil-red-O (Sigma-Aldrich) was dissolved in isopropanol. Oil-red-O stock solution and $H_2O$ were mixed at a ratio of 6:4 and filtered. Then 60% Oil-red-O stock solution was incubated with the cells for 1 h and washed with distilled water and scanned for image.

Establishment of preadipocyte cell line stably expressing Sh-Con, Sh-Nedd8-I and II, sh-APPBP-I and II, pLVX-IRES-puro-Con, pLVX-IRES-puro-His-NEDD8

To prepare stable preadipocyte cell lines 3T3-L1 and 3T3-F442A cells, a packaging cell line HEK293T cells were co-transfected with pLKO.1-puro (Sigma-Aldrich) lentiviral plasmid vector and a matching packaging plasmid. And the supernatant was collected after 2 days of the transfection and then used to infect 3T3-L1 and 3T3-F442A cells, which were then incubated in the presence of puromycin after 2 days to select stably transfected cells.

TABLE 3

| Target Genes | Sequences (5' to 3'): Sense and Antisense strands | SEQ ID NOs |
|---|---|---|
| mouse NEDD8-I | 5'-AUUAAAAAUUGAUUCGCUCCACCUUGUCUC UCGAGAGACAAGGUGGAGCGAAUCAA-3' | SEQ ID NO: 10 |
| mouse NEDD8-II | 5'-AUUAAAAAACUUUAAUUAGCAUCUUCUUCC UCGAGGAAGAAGAUGCUAAUUAAAGU-3' | SEQ ID NO: 11 |
| mouse APPBP1-I | 5'-AUUAAAAACAGAUUCCAAAGCUUCUUGUCC UCGAGGACAAGAAGCUUUGGAAUCUG-3' | SEQ ID NO: 12 |

TABLE 3-continued

| Target Genes | Sequences (5' to 3'): Sense and Antisense strands | SEQ ID NOs |
|---|---|---|
| mouse APPBP1-II | 5'-AAUUAAAAAUAAAUUUCCUUGACCCUCCUU CUCGAGAAGGAGGGUCAAGGAAAUUUA-3' | SEQ ID NO: 13 |
| Non-target (GFP) | 5'-AAUUAAAAACGUGAUCUUCACCGACAAGAU CUCGAGAUCUUGUCGGUGAAGAUCACG-3' | SEQ ID NO: 14 |

In the table, the second column from the left indicates gene identification number from which each siRNA was originated.

Animal Experiment, Grafting of 3T3-L1, 3T3-F442A Preadipocytes and Analysis of Fat Pads.

The animal experiment was approved by the Seoul National University Animal Experiments Ethics Committee (Institutional Animal Care and Use Committee: SNUI-ACUC) (SNU-110718-1). 3T3-L1 and 3T3-F442A cells stably expressing pLKO.1-puroshControl or pLKO.1-puro-shNEDD8 were trypsinized and suspended in DMEM supplemented with 10bovine serum. The cells (3×10⁷ cells) were injected into the subcutis of the abdomens of 9-week old male BALB/c nude mice (Orient Bio. Inc., Korea). After 5 weeks, fat pads from the implanted preadpocytes were fixed with formalin and stained with hematoxylin and eosin and examined under microscope.

Immunofluorescence

Fat tissues were fixed with formalin and sectioned into 4-μm slices. The sections were deparaffinized and hydrated, and antigens were then retrieved by heating the specimens in 10 mM sodium citrate buffer (pH 6.0) in a microwave for 20 min. After blocking, the specimens were incubated overnight at 4° C. with anti-perilipin (1:500) and then with Alexa Fluor® 488 anti-IgG antibody (Invitrogen) for visualization for 1 h. Nuclei were stained with DAPI (1:5000 in PBS, Sigma Aldrich). Then the stained fat tissues were examined under microscope (400×).

Statistical Analysis.

Means, standard deviations (SD) and standard errors of the mean (SEM) were calculated using Microsoft® Excel 2007. MannWhitney U test was used for statistical analysis.

Example 1

Increase of NEDD8 Expression Associated with Adipocyte Differentiation

Figure 1B:
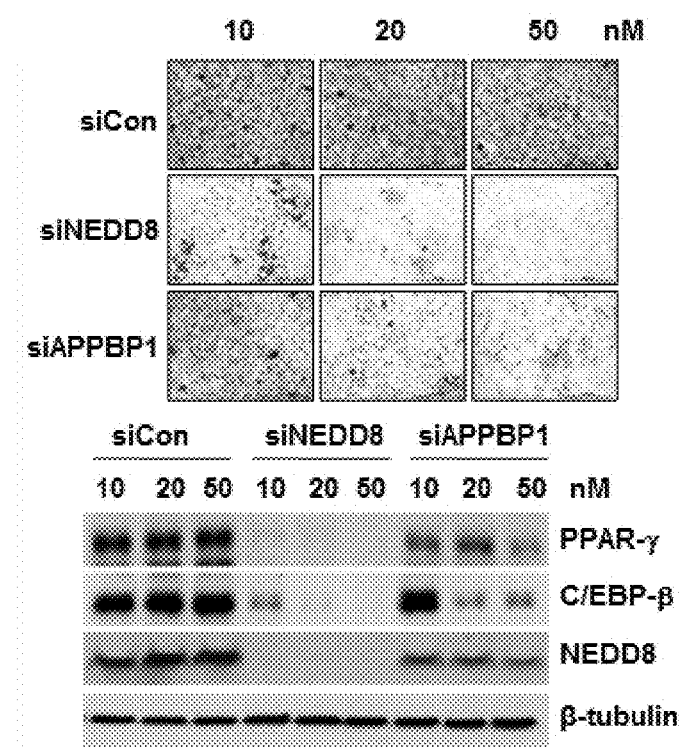
Figure 1C:
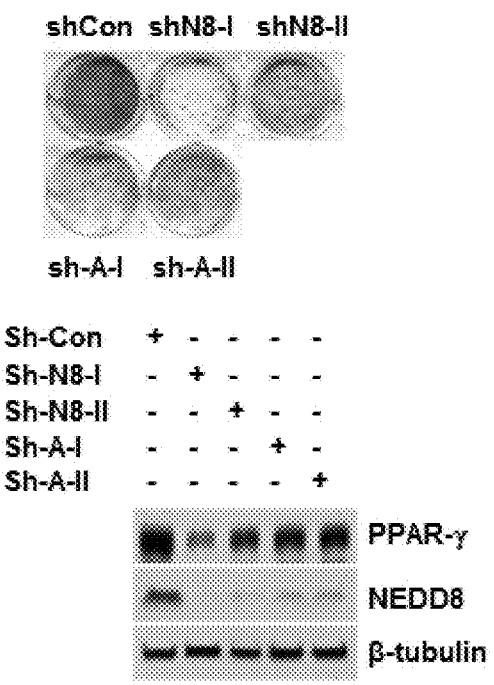
Figure 1D:
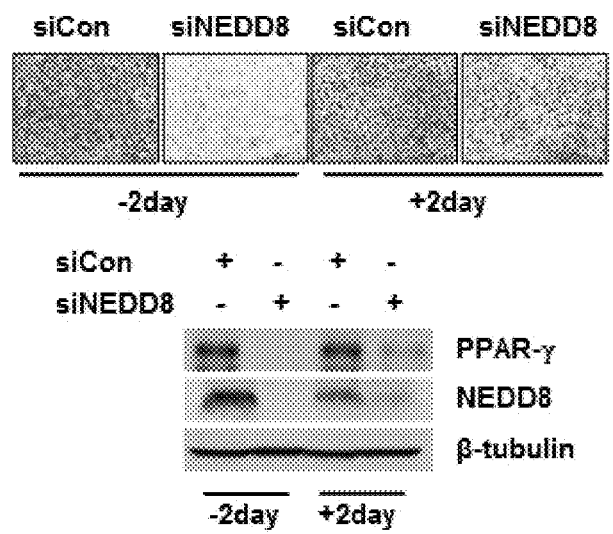
Figure 1D:
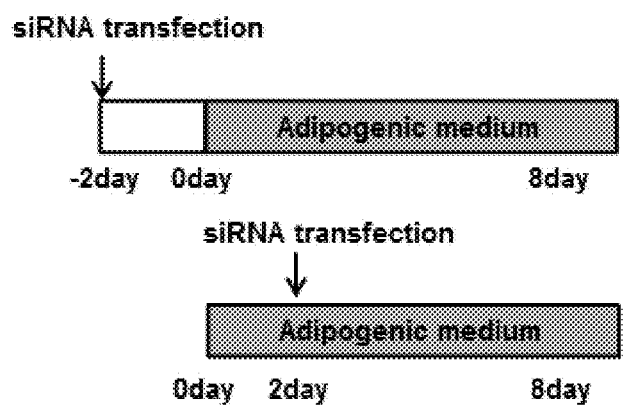
Figure 1E:
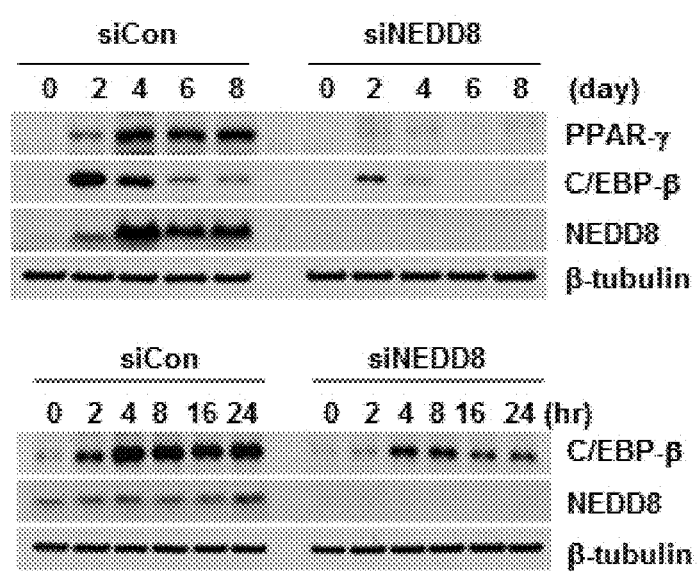
FIG. 1E is the results of western blotting showing the effect of NEDD8 on the expression of PPAR-v and C/EBP-β in which the cells were transfected with siControl and siNEDD8 before the adipose differentiation and analyzed at 0, 2, 5, 6, and 8 days after the adipose differentiation was induced.
Figure 1F:
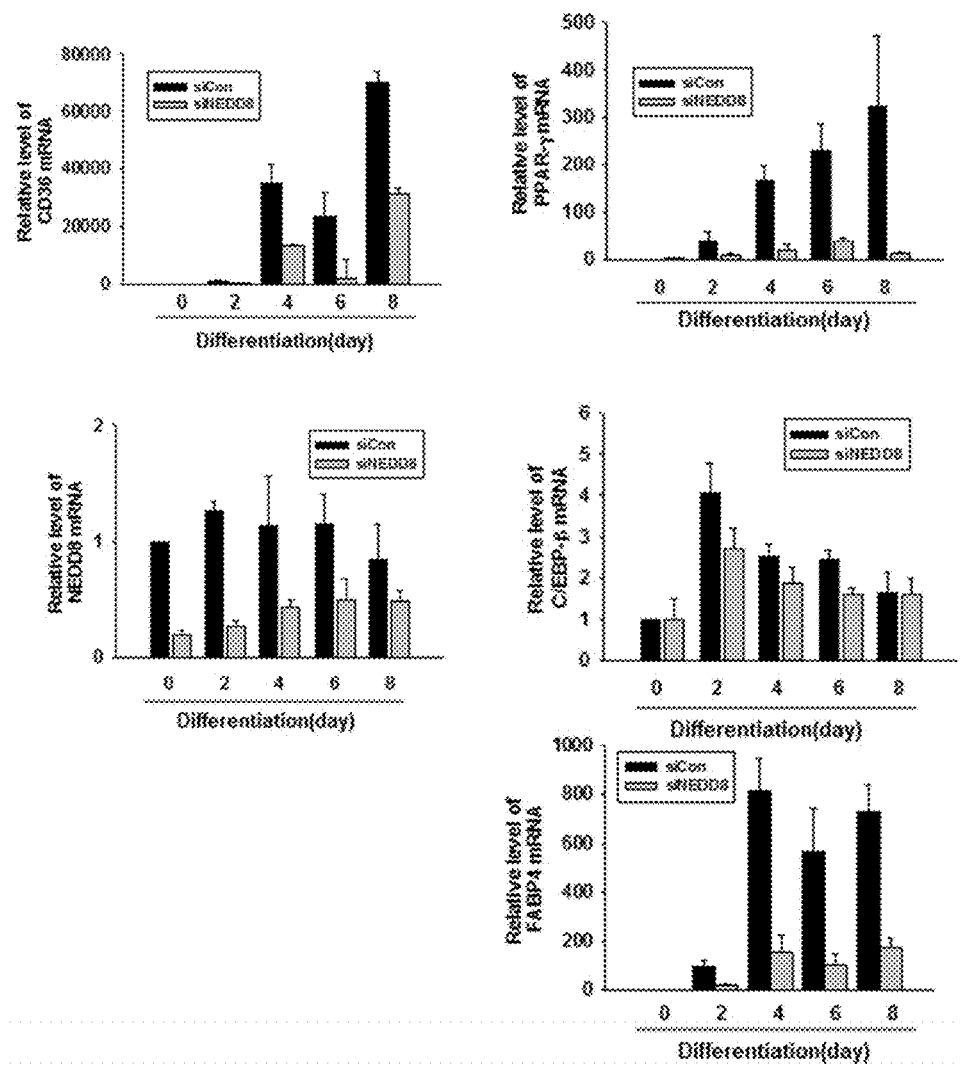
FIG. 1F is the results RT-PCR showing the effect of NEDD8 on the expression of PPAR-v, C/EBP-β, CD36, FABP4 and NEDD8 at the mRNA level in which the cells were transfected with siControl and siNEDD8 before the transfection and analyzed at 0, 2, 5, 6, and 8 days after the adipose differentiation was induced.

To identify the role of NEDD8 in the differentiation of preadipocyte into adipocyte, preadipocyte 3T3-L1 cells were incubated in DMI mixture (1 μM dexamethasone, 500 μM 3-isobutyl-a-methylxanthine (IBMX), 5 μg/ml insulin). The expression level of NEDD8 was confirmed by Oil-red O staining and western blot (FIG. 1A, upper panel). The expression level of NEDD8 protein was found to be increased from 3 days after the differentiation was induced (FIG. 1A lower panel). Also the factors PPAR-v, C/EBP-α, β, δ, which are important for adipogenesis were also found to be increased (FIG. 1A lower panel). NEDD8, a substrate of neddylation, is conjugated to target proteins in a cascade of E1-E2-E3 enzymes. When E1 enzyme APPBP1 and substrate NEDD8 were knocked down by siRNAs transfected into the cells two days before the differentiation is induced, it was found that the adipogenesis is suppressed (FIG. 1B). The suppression of adipogenesis was confirmed again by shAPPBP1, shNEDD8 stable knock-down 3T3-L1 cells which were established using pLKO.1-puro lentiviral plasmid vector system (FIG. 1C). To examine the effect of NEDD8 on the adipogenesis after the differentiation is initiated, NEDD8 was knock down using siNEDD8 after the cells were induced to differentiation. As a result, it was found that the adipogenesis was suppressed by a knock down of NEDD8 by siNEDD8 even after the differentiation is initiated. Further it was shown that the expression of PPAR-v was also suppressed (FIG. 1D). When the cells were induced to differentiation after NEDD8 had been knock down using RNAi system and examined for any changes at 0, 2, 4, 6 and 8 days during the differentiation, it was found that the expression of PPAR-v and C/EBP-β which are factors involved in adipogenesis was decreased compared to the control in a time dependent manner (FIG. 1E). C/EBP-β is expressed at early stage of the differentiation, and thus the expression was examined at 0, 2, 4, 8, 16, 24 h after the initiation of differentiation. The expression of C/EBP-β was decreased by siNEDD8 (FIG. 1E). Also the mRNA expression levels of PPAR-v, C/EBP-β, FABP4, and CD36 which are major marker for adipogenesis were found to be decreased by siNEDD8 knock down, which were analyzed by PCR at 0, 2, 4, 6, and 8 days after the start of differentiation (FIG. 1F). These results indicate that the neddylation of PPAR-v play an essential role in the adipogenesis. It was found in the present disclosure that suppression of any one of the process involved in the neddylation may lead to the suppression of adipogenesis. Thus the differentiation of adipocyte can be inhibited or suppressed by inhibiting the enzyme reactions involved in the neddylation process or the expression of any one of the proteins involved in the enzyme reactions by use of a proper drug.

Example 2

Suppression of Adipogenesis by MLN4924 (NEDDylation E1 Enzyme Inhibitor)

Neddylation is the post-translational modification in which NEDD8 is conjugated to a target protein by E1 activating enzyme (NAE; heterodimer of NAE1 and UBA3 subunit), E2 conjugating enzyme (Ubc12, UBE2M) and E3 ligase (Gong et al., J. Biol. Chem. 1999; 274:12036-12042). MLN4924 is known as an inhibitor of NEDD8 E1 activating enzyme (Teresa et al. Nature 2008; 458; 732-736).

Figure 2A:
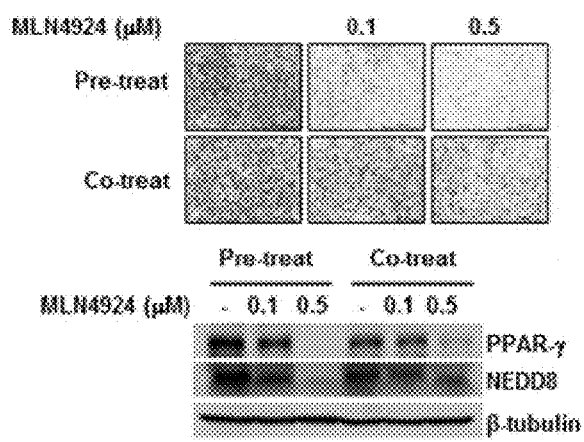
FIGS. 2A and 2B show that the differentiation of 3T3L1 cells into adipocytes was suppressed when the cells were treated with an inhibitor of E1 enzyme involved in the neddylation, MLN4924.
Figure 2B:
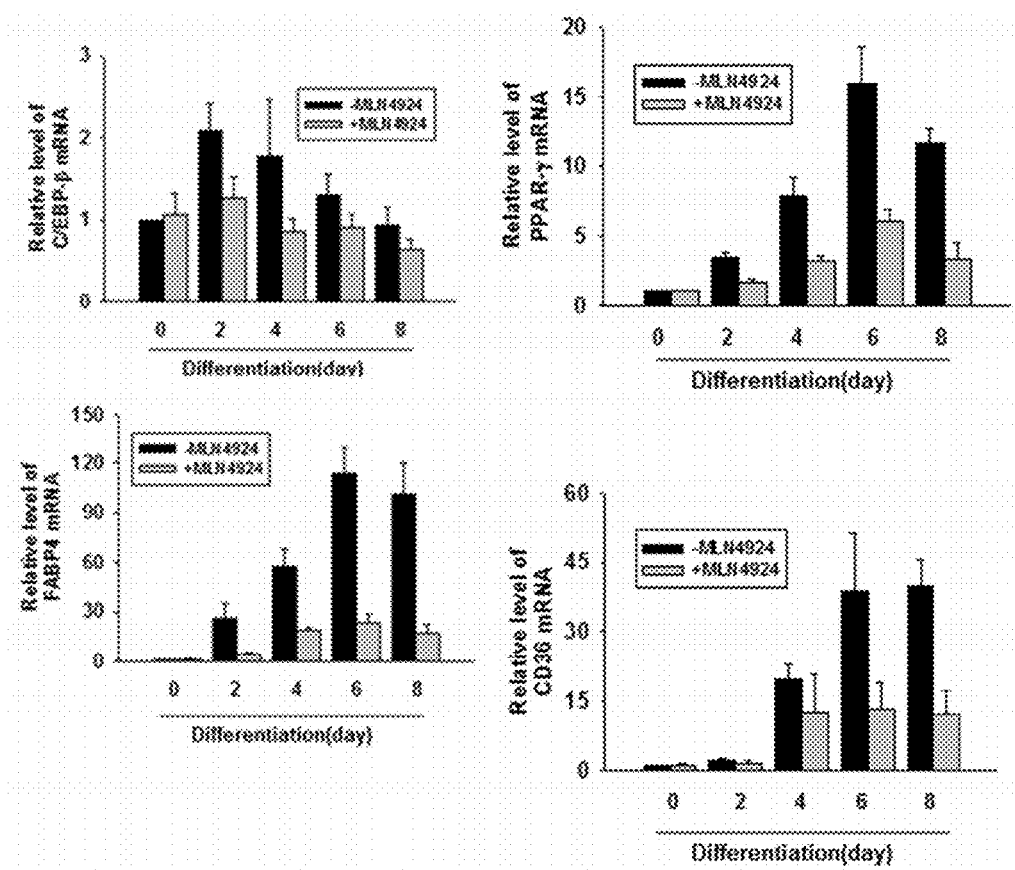

The effect of MLN4924 on the differentiation of adipocyte was examined by treating 3T3-L1 cells with MLN4924 before and after the differentiation. As a result, it was found in the present disclosure that MLN4924 suppresses the expression of PPAR-v protein when the cells were treated after the differentiation was induced (FIG. 2A). When the cells were treated before the differentiation, it was found that PPAR-v, C/EBP-β, FABP4, and CD36 were decreased at the mRNA level (FIG. 2B). This indicates that MLN4924 can be advantageously used to treat or prevent obesity.

Example 3

PPAR-stabilization by Suppression of PPAR-v Ubiquitination by NEDD8

The expression of PPAR-v protein is regulated by phosphorylation, sumoylation, and post-translational modification such as ubiquitination (van Beekum. Obesity (Silver Spring) 2009; 17; 213-219). Particularly, it is known that PPAR-v is degraded by proteasome due to polyubiquination (Floyd Z E et al. J Biol Chem. 2002; 277:4062-4068).

Figure 3A:
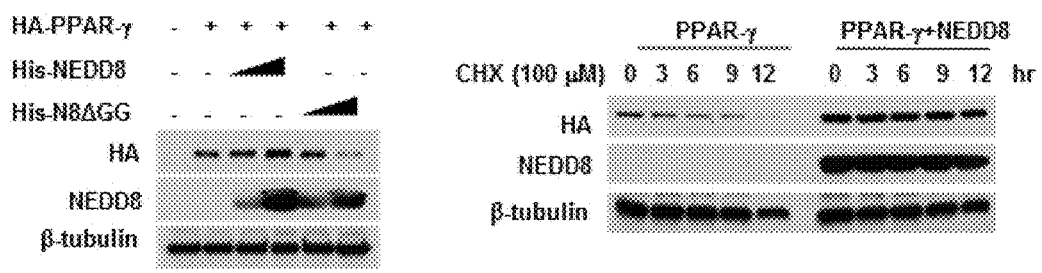
Figure 3B:
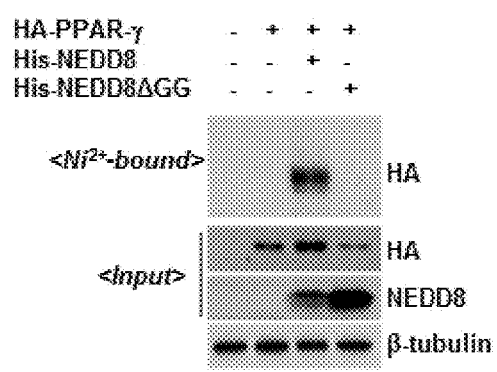
Figure 3B:
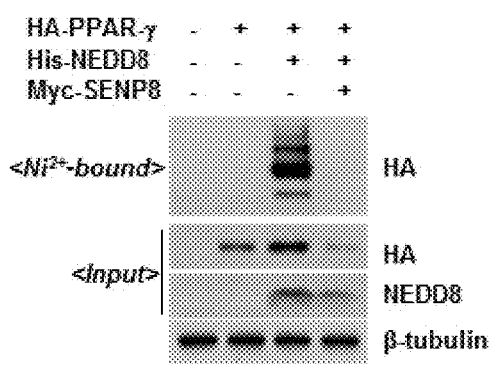

In the present disclosure, it was found that the level of PPAR-v protein was increased by NEDD8 in HEK293 cells, but the increase disappeared by the mutant NEDDD8ΔGG which cannot be neddylated (FIG. 3A left panel). When synthesized PPAR-v was treated with cyclohexamide for 0, 3, 6, 9, 12 h to compare the stability of PPAR-v, PPAR-v was found to be stabilized by NEDD8 overexpression (FIG. 3A right panel). It was confirmed that the results are due to the neddylation of PPAR-v using $Ni^{2+}$ pull down assay under denaturing condition, in which NEDD8 was covalently conjugated to PPAR-v using $Ni^{2+}$ pull down assay under denaturing condition. The conjugation was not observed with conjugation deficient mutant NEDDΔGG (FIG. 3B upper panel). Further the covalent conjugation between PPAR-v and NEDD8 was not observed by deneddylation enzyme SENP8 (FIG. 3B lower panel).

Then the neddylation of endogenous PPAR-v was analyzed in 3T3-L1 stably expressing His-NEDD8 prepared by pLVX-IRES virus infection system. As a result, it was shown that the endogenous PPAR-v is neddylated. However the other major transcription factors involved in the adipogenesis, C/EBP-α, β and δ were not found to be neddylated (FIG. 3C).

Figure 3D:
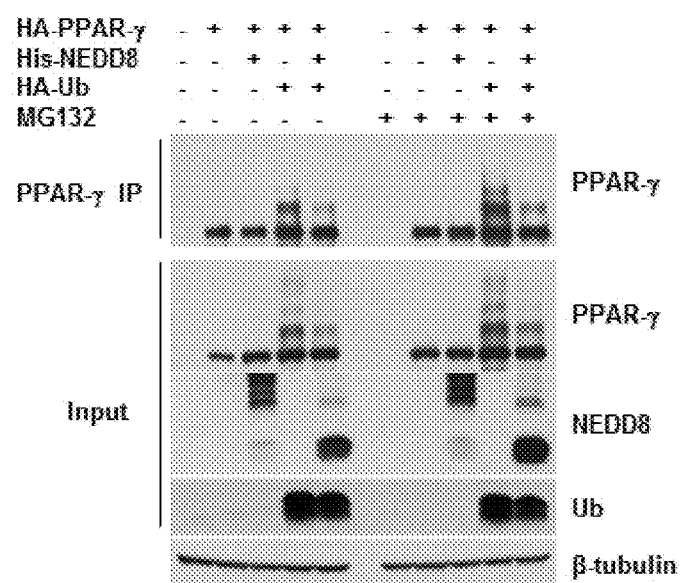
Figure 3E:
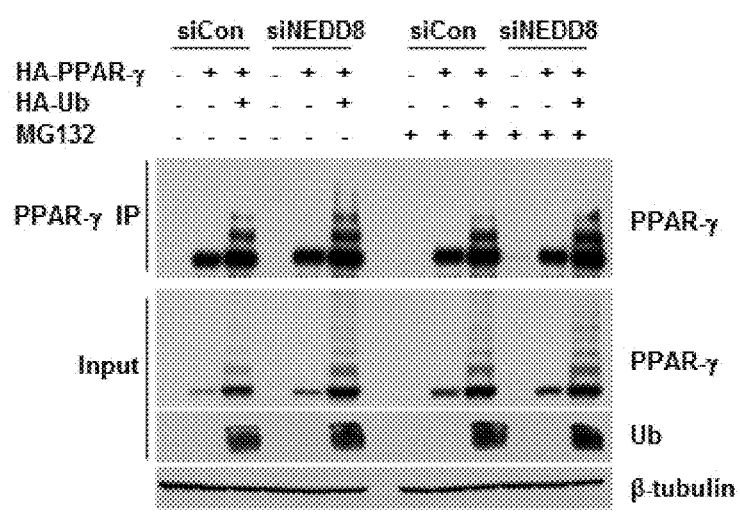

Then, it was also confirmed that PPAR-v is stabilized by neddylation which inhibits the ubiquitination of PPAR-v. That is, when PPAR-v and Ub DNA were overexpressed in HEK293 cells, the ubiquitinated PPAR-v was increased, which however was decreased by the overexpression of NEDD8 (FIG. 3D). In contrast, the ubiquitination of PPAR-v was shown to be increased by siNEDD8 (FIG. 3E). These results indicate that the neddylated PPAR-v is stabilized by inhibiting the protein degradation by ubiquitination.

Example 4

Identification of Neddylated Domain of PPAR-v

PPAR-v is consist of N-terminal trans-activating domain (AF1, NT), well conserved DNA binding domain (DBD, M), and C-terminal ligand binding domain (LBD, CT) (Maryam Ahmadian. Nature Medicine 2013;99:557566).

Figure 4A:
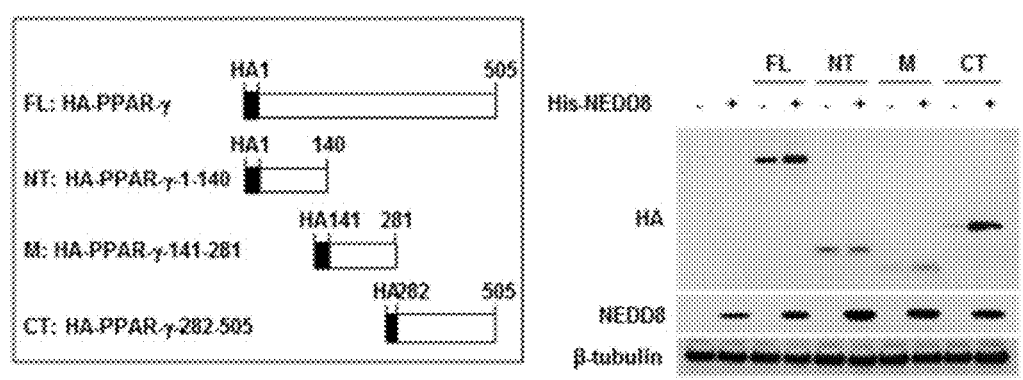
FIGS. 4A to 4C show the results of the assays to identify the regions of PPAR-v and NEDD8 interacting each other.
Figure 4B:
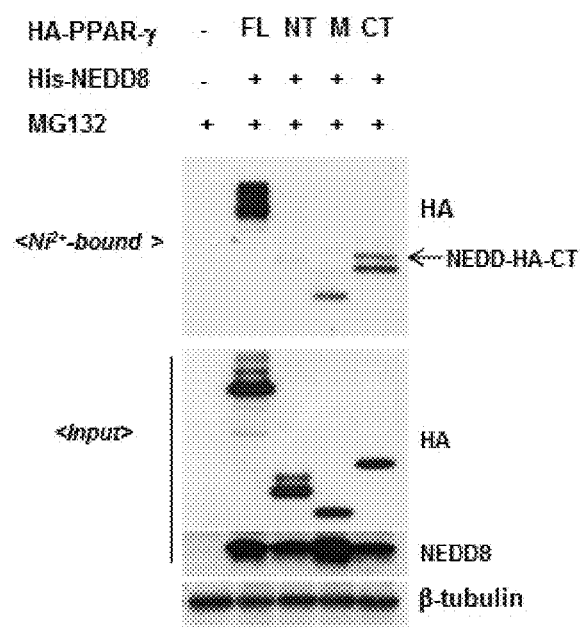
Figure 4C:
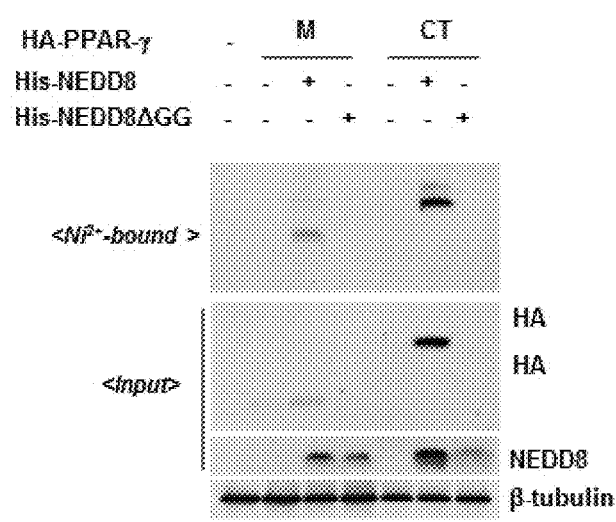

When HEK293 cells were transfected with PPAR-v full-length (FL), NT, M, CT together with NEDD8, it was found that the level of M, CT domain except NT is increased (FIG. 4A). Also, the $Ni^{2+}$ pull-down assay under denaturing condition showed that PPAR-v is neddylated at M, CT (FIG. 4B). When NEDD8ΔGG was employed, the neddylation of PPAR-v at M, NT was not observed (FIG. 4C). The results indicate that PPAR-v is neddylated at the DNA-binding domain (DBD) and ligand binding domain (LBD).

Example 5

Identification of E3 Ligase of PPAR-v

MDM-2 (murine double minute 2) is known as ubiquitin E3 ligase of p53 (Reiko Honda et al. FEBS Letters 1997; 420:25-27). It is also shown that its expression is increased in preadipocyte 3T3-L1 (Berberich S J et al. Differentiation 1999; 64: 205-212) and it activates CREB to promote the adipogenesis (P Hallenborg et al. Cell Death and Differentiation 2012; 19:1381-1389).

Figure 5A:
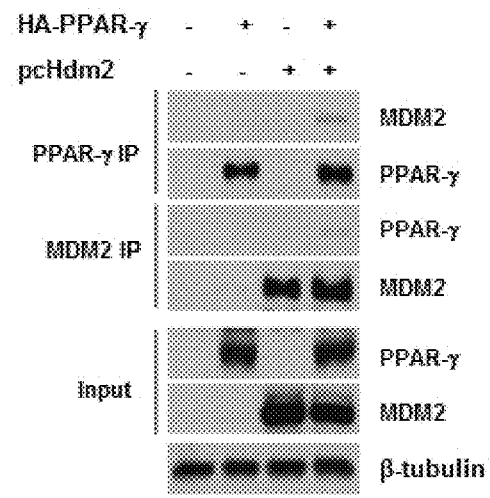
FIGS. 5A to 5D show that E3 ligase of PPAR-v is MDM2.
Figure 5B:
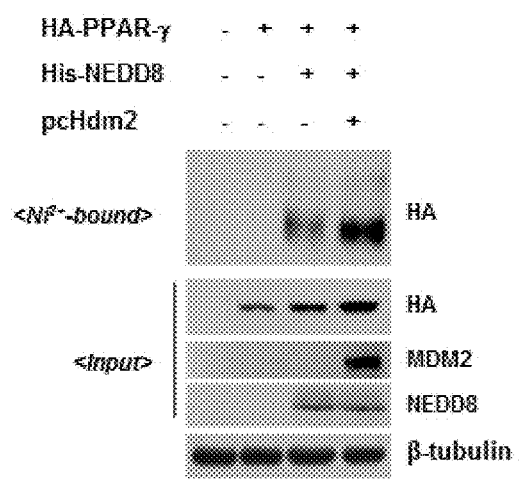

The E3 ligase involved in the neddylation of PPAR-v in HEK293 cells has been identified in the present disclosure. For this, MDM2 cDNA vector and PPAR-v expression vector were contransfected into the cells and they were detected using antibodies against PPAR-v and MDM2 in a coimmunopercipitation assay. As a result, it was shown that they directly bind to each other (FIG. 5A). It also has been found that MDM2 that interacts with PPAR-v is an E3 ligase that mediates the neddylation of PPAR-v (FIG. 5B).

Figure 5C:

When siMDM2 was transfected into preadipocyte 3T3-L1 cells, it has been shown that the differentiation is suppressed in a manner dependent on the amount of siMDM2 used (FIG. 5C).

Figure 5D:
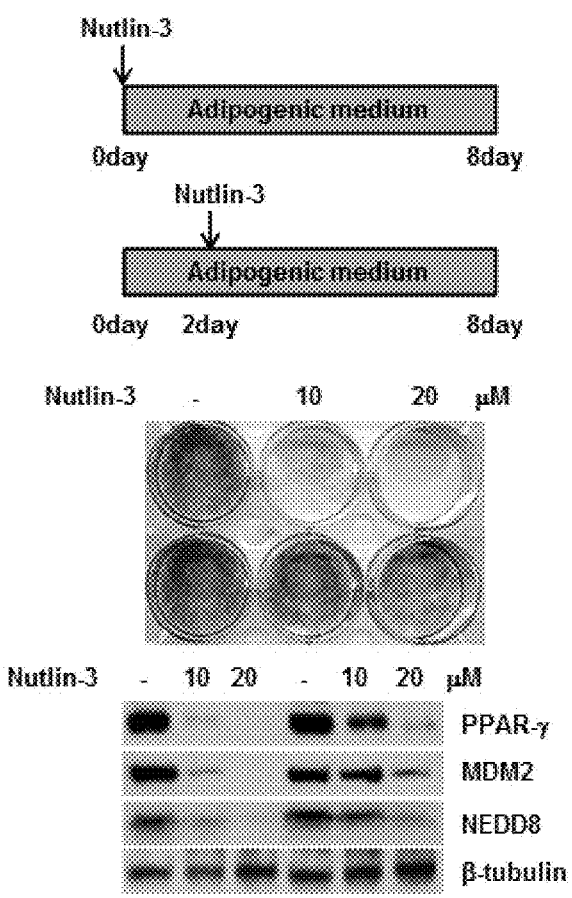

Further it also has been shown that the differentiation is suppressed by nutlin-3 which is a MDM2 suppressor in a manner dependent on the amount transferred (FIG. 5D).

These results indicate that PPAR-v is stabilized through the neddylation by MDM2 and thus induces the adipogenesis.

Example 6

Determination of the Importance of NEDD8 in the Adipogenesis In Vivo

Figure 6A:
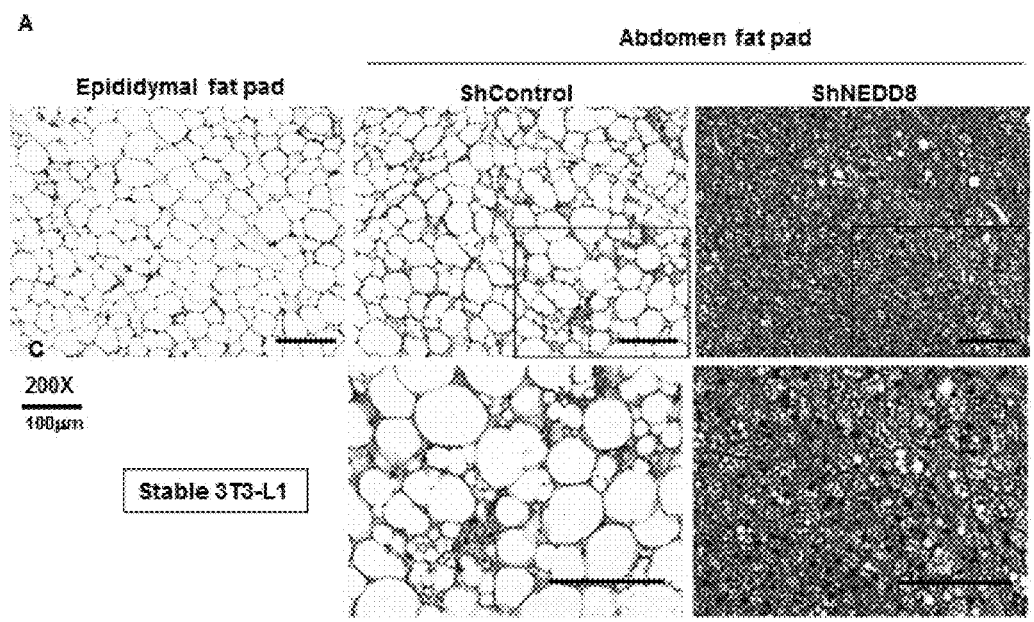
FIGS. 6A to 6C show that NEDD8 is required for the adipose differentiation in vivo.
Figure 6B:
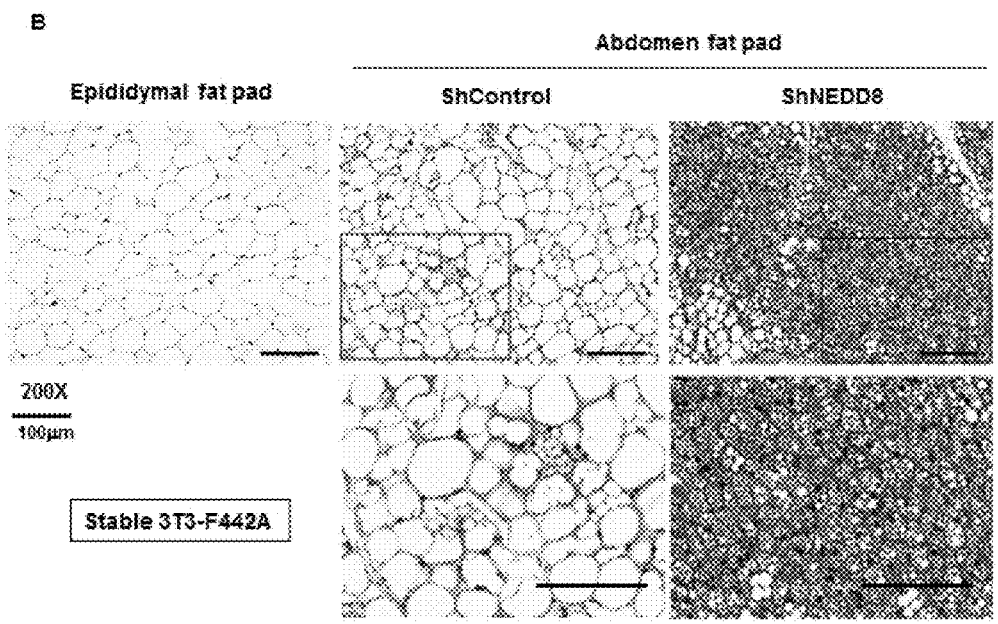

The role of NEDD8 in the adipogenesis was determined in vivo. For this, shControl or shNEDD8 expression vectors were constructed using a lentiviral plasmid vector pLKO.1-puro (Sigma-Aldrich). The expression vector was then used for transfection into 3T3-L1, 3T3-F442A cells to establish a stable cell line in which NEDD8 was knock down. Then the preadipocyte cells expressing ShControl or shNEDD8 as above were injected intraperitoneally into mice. After 5 weeks, the fat pads were isolated and stained with H&E. As a result, it has been found that the adipogenesis is suppressed in 3T3-L1, 3T3-F442A cells expressing shNEDD8 compared to the control expressing shControl in which the cells are differentiated into adipocyte (FIGS. 6A and B).

Figure 6C:
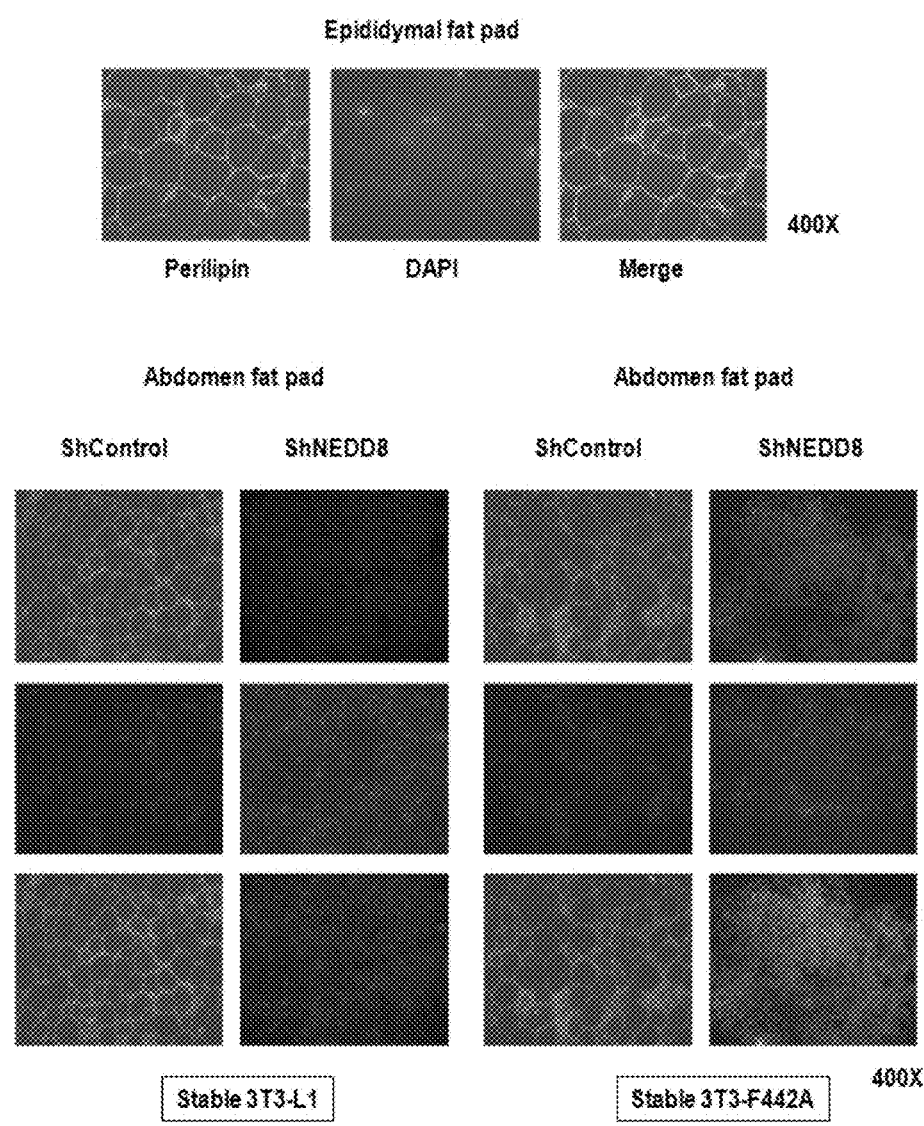

Further to confirm that the adipogenesis as shown above is from a normal process, the differentiation into adipocyte was also examined in the fat pad from epididymis. For this, the immunofluorescence was performed on the lipid droplet scaffold protein perilipin, As a result, it has been found that the lipid droplet is not formed in the fat pad from the mouse injected with shNEDD8 expression cells compared to the controls injected with shControl expression cells in which the lipid droplet is normally formed (FIG. 6C).

These results indicate that NEDD8 also plays an important role in the adipogenesis in vivo and thus the inhibitors of neddylation can be advantageously used to prevent or treat obesity based on the result that the decrease in the expression of NEDD8 results in the suppress the adipogenesis.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

What is claimed is:

1. A method of suppressing an adipose differentiation comprising administering to a subject in need thereof a therapeutically effective amount of an inhibitor of a neddylation pathway of PPAR (Peroxisome Proliferator Activated Receptor)-gamma, wherein the inhibitior of a neddylation pathway of PPAR-gamma suppresses activity or expression of at least one protein selected from the group consisting of a NEDD8(Neural precursor cell-Expressed Developmental Downregulation 8) and an E1 enzyme NAE(NEDD8 Activating Enzyme E1 regulatory subunit).

2. The method of claim 1, wherein the inhibitor of a neddylation pathway of PPAR-gamma is at least one selected from the group consisting of a small molecule of MLN4924, an antibody, an antisense oligonucleotide, a siRNA, a shRNA, and a miRNA.

3. The method of claim 2, wherein the NEDD8 inhibitor is a siRNA having a nucleic acid sequence selected from the group consisting of SEQ ID NOs: 1, 2 and 3; or a shRNA having a nucleic acid sequence selected from SEQ ID NOs: 10 or 11; the NAE inhibitor is a siRNA having a nucleic acid sequence selected from the group consisting of SEQ ID NOs: 4, 5 and 6; or a shRNA having a nucleic acid sequence selected from SEQ ID NOs: 12 or 13.

4. A method of treating obesity comprising administering a therapeutically effective amount of an inhibitor of neddylation of PPAR-gamma to a subject in need of treatment, wherein the inhibitor of neddylation of PPAR-gamma is an inhibitor of a NEDD8, or an E1 enzyme NAE.

5. The method of claim 4, wherein the inhibitor of the NEDD8 or NAE is an agent that inhibits the expression or activity thereof and is selected from the group consisting of a small molecule of MLN4924, an antibody, an antisense oligonucleotide, a siRNA, a shRNA, and a miRNA.

6. The method of claim 5, wherein the NEDD8 inhibitor is a siRNA having a nucleic acid sequence selected from the group consisting of SEQ ID NOs: 1, 2 and 3; or a shRNA having a nucleic acid sequence selected from SEQ ID NOs: 10 or 11; and the NAE inhibitor is a siRNA having a nucleic acid sequence selected from the group consisting of SEQ ID NOs: 4, 5 and 6; or a shRNA having a nucleic acid sequence selected from SEQ ID NOs: 12 or 13.

* * * * *